(12) United States Patent
Kosmatopoulos et al.

(10) Patent No.: US 7,425,606 B2
(45) Date of Patent: Sep. 16, 2008

(54) METHOD FOR SCREENING PEPTIDES FOR USE IN IMMUNOTHERAPY

(75) Inventors: Kostas Kosmatopoulos, Paris (FR); Sophie Tourdot, Chaumontel (FR); Antonio Scardino, Paris (FR); Alexandre David Gross, Paris (FR)

(73) Assignees: Institut National de la Sante et de la Recherche Medicale (Inserm) (FR); Institut Gustave Roussy (IGR) (FR)

( * ) Notice: Subject to any disclaimer, the term of this patent is extended or adjusted under 35 U.S.C. 154(b) by 575 days.

(21) Appl. No.: 10/333,430

(22) PCT Filed: Jul. 20, 2001

(86) PCT No.: PCT/FR01/02387

§ 371 (c)(1),
(2), (4) Date: Oct. 2, 2003

(87) PCT Pub. No.: WO02/08716

PCT Pub. Date: Jan. 31, 2002

(65) Prior Publication Data

US 2004/0072240 A1    Apr. 15, 2004

(30) Foreign Application Priority Data

Jul. 21, 2000    (FR) .................................. 11 09591

(51) Int. Cl.
    *C07K 2/00*    (2006.01)
(52) U.S. Cl. ..................................................... 530/300
(58) Field of Classification Search ................. 530/300; 424/184.1
    See application file for complete search history.

(56) References Cited

U.S. PATENT DOCUMENTS

2004/0086518 A1*    5/2004    Zanetti ..................... 424/185.1

FOREIGN PATENT DOCUMENTS

| WO | WO 91/04045 | 4/1991 |
| WO | WO 95/27901 | 10/1995 |
| WO | WO 97/35193 | 9/1997 |
| WO | WO 00/02581 | 1/2000 |

OTHER PUBLICATIONS

Plotkin et al (Vaccines W.B. Saunders Company 1988, p. 571).*
Ezzell (J. NIH Res, vol. 7, pp. 46-49, 1995).*
Spilter (Cancer Biotherapy vol. 10, pp. 1-3, 1995).*
Boon (Adv. Can. Res. vol. 58, pp. 177-210, 1992).*
Gura (Science vol. 278, pp. 1041-1042, 1997).*
Lee et al (Journal of Immunology vol. 163, pp. 6292-6300, 1999).*
Pogue et al., "Amino-terminal alternation of the HLA-A*0201-restricted human immunodeficiency virus pol peptide increases complex stability and in vitro immunogenicity", *Proceedings of the National Academy of Sciences of the United States*, vol. 92, No. 18, 1995, pp. 8166-8170.
Hudrisier et al., "Relative implication of peptide residues in binding to major histocompatibility complex class I, H-2D-b: Application to the design of high-affinity, allele-specific peptides", *Molecular Immunology*, vol. 32, No. 122, 1995, pp. 895-907.
Oukka et al., "Protection against lethal viral infection by vaccination with nonimmunodominant peptides", *Journal of Medicine*, vol. 157, No. 7, Oct. 1, 1996, pp. 3039-3045.
Tourdot et al., "Chimeric peptides: a new approach to enhancing the immunogenicity of peptides with low MHC class I affinity: application in antiviral vaccination", *Journal of Immunology*, vol. 159, No. 5, Sep. 1, 1997, pp. 2391-2398.

* cited by examiner

*Primary Examiner*—Mark Navarro
(74) *Attorney, Agent, or Firm*—Alston & Bird LLP

(57) ABSTRACT

Identifying subdominant/cryptic epitopes (I) that are presented by a HLA (human leukocyte antigen) Class I molecule, is new. Identifying subdominant/cryptic epitopes (I) that are presented by a HLA (human leukocyte antigen) Class I molecule comprising selecting at least one peptide (II) of 8-11 amino acids (aa), potentially representing an epitope for Class I presentation, from a protein against which a cytotoxic T cell (CTL) response is to be raised. (II) corresponds to a non-immunogenic peptide with low affinity for Class I molecules. Variants (IIa) of (II) are prepared in which the N-terminal aa is replaced by Tyr and their immunogenicity detected by identifying those that generate a CTL response against target cells expressing the parent protein. Peptide sequences from which active (IIa) are derived are then identified. Independent claims are also included for the following: (1) immunogenic peptide epitopes (IIa) derived from (I) identified this way; and (2) nucleic acid (III) that encodes chimeric polypeptides (IV) containing one or more, same or different, copies of (IIa).

7 Claims, 18 Drawing Sheets

SEQUENCE LISTING

```
<160> NUMBER OF SEQ ID NOS: 70

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Ser Met Ile Glu Asn Leu Glu Tyr Met
```

```
<210> SEQ ID NO 2
<211> LENGTH: 9
<212> TYPE: PRT
<213> ORGANISM: Artificial sequence
<220> FEATURE:
<221> NAME/KEY: VARIANT
<222> LOCATION: (2)
<223> OTHER INFORMATION: Xaa(1) = Tyr or Lys and Xaa(4) = Glu or Lys
<220> FEATURE:
<223> OTHER INFORMATION: Synthetic peptide

<400> SEQUENCE: 2

Xaa Ala Ile Xaa Asn Ala Glu Ala Leu
  1               5

<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Ile Val Gly Ala Glu Thr Phe Tyr Val
  1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide

<400> SEQUENCE: 4

Pro Leu Thr Ser Ile Ile Ser Ala Val
  1               5

<210> SEQ ID NO 5
<211> LENGTH: 9
<212> TYPE: PRT
<213> ORGANISM: Artificial sequence
<220> FEATURE:
<223> OTHER INFORMATION: Synthetic peptide

<400> SEQUENCE: 5

Ala Leu Ile His His Asn Thr His Leu
  1               5

<210> SEQ ID NO 6
<211> LENGTH: 9
<212> TYPE: PRT
<213> ORGANISM: Artificial sequence
<220> FEATURE:
<223> OTHER INFORMATION: Synthetic peptide

<400> SEQUENCE: 6

Thr Leu Glu Glu Ile Thr Gly Tyr Leu
  1               5

<210> SEQ ID NO 7
<211> LENGTH: 9
<212> TYPE: PRT
<213> ORGANISM: Artificial sequence
<220> FEATURE:
<223> OTHER INFORMATION: Synthetic peptide
```

```
<400> SEQUENCE: 7

Pro Leu Gln Pro Glu Gln Leu Gln Val
  1               5

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

Glu Met Met Thr Ala Cys Gln Gly Val
  1               5

<210> SEQ ID NO 9
<211> LENGTH: 10
<212> TYPE: PRT
<213> ORGANISM: Artificial sequence
<220> FEATURE:
<223> OTHER INFORMATION: Synthetic peptide

<400> SEQUENCE: 9

Leu Leu Asp Thr Gly Ala Asp Asp Thr Val
  1               5                  10

<210> SEQ ID NO 10
<211> LENGTH: 9
<212> TYPE: PRT
<213> ORGANISM: Artificial sequence
<220> FEATURE:
<223> OTHER INFORMATION: Synthetic peptide

<400> SEQUENCE: 10

Arg Leu Phe Phe Tyr Arg Lys Ser Val
  1               5

<210> SEQ ID NO 11
<211> LENGTH: 10
<212> TYPE: PRT
<213> ORGANISM: Artificial sequence
<220> FEATURE:
<223> OTHER INFORMATION: Synthetic peptide

<400> SEQUENCE: 11

Asp Leu Gln Val Asn Ser Leu Gln Thr Val
  1               5                  10

<210> SEQ ID NO 12
<211> LENGTH: 10
<212> TYPE: PRT
<213> ORGANISM: Artificial sequence
<220> FEATURE:
<223> OTHER INFORMATION: Synthetic peptide

<400> SEQUENCE: 12

Lys Leu Thr Gly Asp Glu Asn Phe Thr Ile
  1               5                  10

<210> SEQ ID NO 13
<211> LENGTH: 10
<212> TYPE: PRT
<213> ORGANISM: Artificial sequence
<220> FEATURE:
<223> OTHER INFORMATION: Synthetic peptide

<400> SEQUENCE: 13
```

```
Phe Leu Pro Trp His Arg Leu Phe Leu Leu
 1               5                  10
```

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

```
Met Leu Leu Ala Val Leu Tyr Cys Leu
 1               5
```

<210> SEQ ID NO 15
<211> LENGTH: 9
<212> TYPE: PRT
<213> ORGANISM: Artificial sequence
<220> FEATURE:
<223> OTHER INFORMATION: Synthetic peptide

<400> SEQUENCE: 15

```
Lys Thr Trp Gly Gln Tyr Trp Gln Val
 1               5
```

<210> SEQ ID NO 16
<211> LENGTH: 10
<212> TYPE: PRT
<213> ORGANISM: Artificial sequence
<220> FEATURE:
<223> OTHER INFORMATION: Synthetic peptide

<400> SEQUENCE: 16

```
Val Leu Tyr Arg Tyr Gly Ser Phe Ser Val
 1               5                  10
```

<210> SEQ ID NO 17
<211> LENGTH: 8
<212> TYPE: PRT
<213> ORGANISM: Artificial sequence
<220> FEATURE:
<223> OTHER INFORMATION: Synthetic peptide

<400> SEQUENCE: 17

```
Thr Asp Gln Val Pro Phe Ser Val
 1               5
```

<210> SEQ ID NO 18
<211> LENGTH: 10
<212> TYPE: PRT
<213> ORGANISM: Artificial sequence
<220> FEATURE:
<223> OTHER INFORMATION: Synthetic peptide

<400> SEQUENCE: 18

```
Ser Leu Ala Asp Thr Asn Ser Leu Ala Val
 1               5                  10
```

<210> SEQ ID NO 19
<211> LENGTH: 10
<212> TYPE: PRT
<213> ORGANISM: Artificial sequence
<220> FEATURE:
<223> OTHER INFORMATION: Synthetic peptide

<400> SEQUENCE: 19

```
Ala Met Leu Gly Thr His Thr Met Glu Val
 1               5                  10
```

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

```
Met Leu Gly Thr His Thr Met Glu Val
 1               5
```

<210> SEQ ID NO 21
<211> LENGTH: 10
<212> TYPE: PRT
<213> ORGANISM: Artificial sequence
<220> FEATURE:
<223> OTHER INFORMATION: Synthetic peptide

<400> SEQUENCE: 21

```
Leu Leu Asp Gly Thr Ala Thr Leu Arg Leu
 1               5                  10
```

<210> SEQ ID NO 22
<211> LENGTH: 9
<212> TYPE: PRT
<213> ORGANISM: Artificial sequence
<220> FEATURE:
<223> OTHER INFORMATION: Synthetic peptide

<400> SEQUENCE: 22

```
Ala Ala Gly Ile Gly Ile Leu Thr Val
 1               5
```

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

```
Ile Leu Thr Val Ile Leu Gly Val Leu
 1               5
```

<210> SEQ ID NO 24
<211> LENGTH: 9
<212> TYPE: PRT
<213> ORGANISM: Artificial sequence
<220> FEATURE:
<223> OTHER INFORMATION: Synthetic peptide

<400> SEQUENCE: 24

```
Cys Leu Thr Ser Thr Val Gln Leu Val
 1               5
```

<210> SEQ ID NO 25
<211> LENGTH: 9
<212> TYPE: PRT
<213> ORGANISM: Artificial sequence
<220> FEATURE:
<223> OTHER INFORMATION: Synthetic peptide

<400> SEQUENCE: 25

```
His Leu Tyr Gln Gly Cys Gln Val Val
```

```
      1               5
```

```
<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Ile Leu Leu Val Val Val Leu Gly Val
  1               5

<210> SEQ ID NO 27
<211> LENGTH: 9
<212> TYPE: PRT
<213> ORGANISM: Artificial sequence
<220> FEATURE:
<223> OTHER INFORMATION: Synthetic peptide

<400> SEQUENCE: 27

Gln Leu Met Pro Tyr Gly Cys Leu Leu
  1               5

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Lys Ile Phe Gly Ser Leu Ala Phe Leu
  1               5

<210> SEQ ID NO 29
<211> LENGTH: 9
<212> TYPE: PRT
<213> ORGANISM: Artificial sequence
<220> FEATURE:
<223> OTHER INFORMATION: Synthetic peptide

<400> SEQUENCE: 29

Val Leu Val Lys Ser Pro Asn His Val
  1               5

<210> SEQ ID NO 30
<211> LENGTH: 9
<212> TYPE: PRT
<213> ORGANISM: Artificial sequence
<220> FEATURE:
<223> OTHER INFORMATION: Synthetic peptide

<400> SEQUENCE: 30

Ala Leu Cys Arg Trp Gly Leu Leu Leu
  1               5

<210> SEQ ID NO 31
<211> LENGTH: 10
<212> TYPE: PRT
<213> ORGANISM: Artificial sequence
<220> FEATURE:
<223> OTHER INFORMATION: Synthetic peptide

<400> SEQUENCE: 31

Val Met Ala Gly Val Gly Ser Pro Tyr Val
  1               5                  10
```

```
<210> SEQ ID NO 32
<211> LENGTH: 9
<212> TYPE: PRT
<213> ORGANISM: Artificial sequence
<220> FEATURE:
<223> OTHER INFORMATION: Synthetic peptide

<400> SEQUENCE: 32

Glu Leu Val Ser Glu Phe Ser Arg Met
 1               5

<210> SEQ ID NO 33
<211> LENGTH: 9
<212> TYPE: PRT
<213> ORGANISM: Artificial sequence
<220> FEATURE:
<223> OTHER INFORMATION: Synthetic peptide e

<400> SEQUENCE: 33

Asn Leu Gln Ser Leu Thr Asn Leu Leu
 1               5

<210> SEQ ID NO 34
<211> LENGTH: 10
<212> TYPE: PRT
<213> ORGANISM: Artificial sequence
<220> FEATURE:
<223> OTHER INFORMATION: Synthetic peptide

<400> SEQUENCE: 34

Leu Leu Gly Cys Ala Ala Asn Trp Ile Leu
 1               5                   10

<210> SEQ ID NO 35
<211> LENGTH: 9
<212> TYPE: PRT
<213> ORGANISM: Artificial sequence
<220> FEATURE:
<223> OTHER INFORMATION: Synthetic peptide

<400> SEQUENCE: 35

Leu Leu Asp Asp Glu Ala Gly Pro Leu
 1               5

<210> SEQ ID NO 36
<211> LENGTH: 9
<212> TYPE: PRT
<213> ORGANISM: Artificial sequence
<220> FEATURE:
<223> OTHER INFORMATION: Synthetic peptide

<400> SEQUENCE: 36

Phe Leu Leu Ser Leu Gly Ile His Leu
 1               5

<210> SEQ ID NO 37
<211> LENGTH: 9
<212> TYPE: PRT
<213> ORGANISM: Artificial sequence
<220> FEATURE:
<223> OTHER INFORMATION: Synthetic peptide

<400> SEQUENCE: 37

Pro Leu Glu Glu Glu Leu Pro Arg Leu
 1               5
```

```
<210> SEQ ID NO 38
<211> LENGTH: 9
<212> TYPE: PRT
<213> ORGANISM: Artificial sequence
<220> FEATURE:
<223> OTHER INFORMATION: Synthetic peptide

<400> SEQUENCE: 38

Gly Ile Leu Gly Phe Val Phe Thr Leu
 1               5

<210> SEQ ID NO 39
<211> LENGTH: 9
<212> TYPE: PRT
<213> ORGANISM: Artificial sequence
<220> FEATURE:
<223> OTHER INFORMATION: Synthetic peptide

<400> SEQUENCE: 39

Ser Leu Tyr Asn Thr Val Ala Thr Leu
 1               5

<210> SEQ ID NO 40
<211> LENGTH: 9
<212> TYPE: PRT
<213> ORGANISM: Artificial sequence
<220> FEATURE:
<223> OTHER INFORMATION: Synthetic peptide

<400> SEQUENCE: 40

Ile Leu Lys Glu Pro Val His Gly Val
 1               5

<210> SEQ ID NO 41
<211> LENGTH: 9
<212> TYPE: PRT
<213> ORGANISM: Artificial sequence
<220> FEATURE:
<223> OTHER INFORMATION: Synthetic peptide

<400> SEQUENCE: 41

Thr Leu Asn Ala Trp Val Lys Val Val
 1               5

<210> SEQ ID NO 42
<211> LENGTH: 9
<212> TYPE: PRT
<213> ORGANISM: Artificial sequence
<220> FEATURE:
<223> OTHER INFORMATION: Synthetic peptide

<400> SEQUENCE: 42

Ala Leu Val Glu Ile Cys Thr Glu Met
 1               5

<210> SEQ ID NO 43
<211> LENGTH: 11
<212> TYPE: PRT
<213> ORGANISM: Artificial sequence
<220> FEATURE:
<223> OTHER INFORMATION: Synthetic peptide

<400> SEQUENCE: 43

Val Leu Asp Val Gly Asp Ala Tyr Phe Ser Val
 1               5                   10
```

```
<210> SEQ ID NO 44
<211> LENGTH: 9
<212> TYPE: PRT
<213> ORGANISM: Artificial sequence
<220> FEATURE:
<223> OTHER INFORMATION: Synthetic peptide

<400> SEQUENCE: 44

Val Ile Tyr Gln Tyr Met Asp Asp Leu
  1               5

<210> SEQ ID NO 45
<211> LENGTH: 9
<212> TYPE: PRT
<213> ORGANISM: Artificial sequence
<220> FEATURE:
<223> OTHER INFORMATION: Synthetic peptide

<400> SEQUENCE: 45

Ile Leu Lys Glu Pro Val His Gly Val
  1               5

<210> SEQ ID NO 46
<211> LENGTH: 9
<212> TYPE: PRT
<213> ORGANISM: Artificial sequence
<220> FEATURE:
<223> OTHER INFORMATION: Synthetic peptide

<400> SEQUENCE: 46

Pro Leu Val Lys Leu Trp Tyr Gln Leu
  1               5

<210> SEQ ID NO 47
<211> LENGTH: 11
<212> TYPE: PRT
<213> ORGANISM: Artificial sequence
<220> FEATURE:
<223> OTHER INFORMATION: Synthetic peptide

<400> SEQUENCE: 47

Glu Ser Glu Leu Val Asn Gln Ile Ile Glu Gln
  1               5                  10

<210> SEQ ID NO 48
<211> LENGTH: 10
<212> TYPE: PRT
<213> ORGANISM: Artificial sequence
<220> FEATURE:
<223> OTHER INFORMATION: Synthetic peptide

<400> SEQUENCE: 48

Glu Leu Val Asn Gln Ile Ile Glu Gln Leu
  1               5                  10

<210> SEQ ID NO 49
<211> LENGTH: 9
<212> TYPE: PRT
<213> ORGANISM: Artificial sequence
<220> FEATURE:
<223> OTHER INFORMATION: Synthetic peptide

<400> SEQUENCE: 49

Leu Leu Trp Lys Gly Glu Gly Ala Val
  1               5

<210> SEQ ID NO 50
```

```
<211> LENGTH: 9
<212> TYPE: PRT
<213> ORGANISM: Artificial sequence
<220> FEATURE:
<223> OTHER INFORMATION: Synthetic peptide

<400> SEQUENCE: 50

Lys Leu Thr Pro Leu Cys Val Ser Leu
  1               5

<210> SEQ ID NO 51
<211> LENGTH: 9
<212> TYPE: PRT
<213> ORGANISM: Artificial sequence
<220> FEATURE:
<223> OTHER INFORMATION: Synthetic peptide

<400> SEQUENCE: 51

Lys Leu Thr Pro Leu Cys Val Thr Leu
  1               5

<210> SEQ ID NO 52
<211> LENGTH: 9
<212> TYPE: PRT
<213> ORGANISM: Artificial sequence
<220> FEATURE:
<223> OTHER INFORMATION: Synthetic peptide

<400> SEQUENCE: 52

Arg Leu Arg Asp Leu Leu Leu Ile Val
  1               5

<210> SEQ ID NO 53
<211> LENGTH: 10
<212> TYPE: PRT
<213> ORGANISM: Artificial sequence
<220> FEATURE:
<223> OTHER INFORMATION: Synthetic peptide

<400> SEQUENCE: 53

Pro Leu Thr Phe Gly Trp Cys Phe Lys Leu
  1               5                  10

<210> SEQ ID NO 54
<211> LENGTH: 9
<212> TYPE: PRT
<213> ORGANISM: Artificial sequence
<220> FEATURE:
<223> OTHER INFORMATION: Synthetic peptide

<400> SEQUENCE: 54

Ala Phe His His Val Ala Arg Glu Leu
  1               5

<210> SEQ ID NO 55
<211> LENGTH: 9
<212> TYPE: PRT
<213> ORGANISM: Artificial sequence
<220> FEATURE:
<223> OTHER INFORMATION: Synthetic peptide

<400> SEQUENCE: 55

Ile Leu Ala Thr Phe Leu Ala Trp Leu
  1               5

<210> SEQ ID NO 56
<211> LENGTH: 10
```

```
<212> TYPE: PRT
<213> ORGANISM: Artificial sequence
<220> FEATURE:
<223> OTHER INFORMATION: Synthetic peptide

<400> SEQUENCE: 56

Phe Leu Phe Trp Leu Met Asp Thr Tyr Val
 1               5                  10

<210> SEQ ID NO 57
<211> LENGTH: 10
<212> TYPE: PRT
<213> ORGANISM: Artificial sequence
<220> FEATURE:
<223> OTHER INFORMATION: Synthetic peptide

<400> SEQUENCE: 57

Gln Leu Leu Arg Ser Phe Phe His Phe Leu
 1               5                  10

<210> SEQ ID NO 58
<211> LENGTH: 9
<212> TYPE: PRT
<213> ORGANISM: Artificial sequence
<220> FEATURE:
<223> OTHER INFORMATION: Synthetic peptide

<400> SEQUENCE: 58

Ser Leu Phe Asp Phe Phe His Phe Leu
 1               5

<210> SEQ ID NO 59
<211> LENGTH: 9
<212> TYPE: PRT
<213> ORGANISM: Artificial sequence
<220> FEATURE:
<223> OTHER INFORMATION: Synthetic peptide

<400> SEQUENCE: 59

Phe Leu Ser Thr Leu Val His Gly Val
 1               5

<210> SEQ ID NO 60
<211> LENGTH: 9
<212> TYPE: PRT
<213> ORGANISM: Artificial sequence
<220> FEATURE:
<223> OTHER INFORMATION: Synthetic peptide

<400> SEQUENCE: 60

Ile Leu Ala Lys Phe Leu His Trp Leu
 1               5

<210> SEQ ID NO 61
<211> LENGTH: 9
<212> TYPE: PRT
<213> ORGANISM: Artificial sequence
<220> FEATURE:
<223> OTHER INFORMATION: Synthetic peptide

<400> SEQUENCE: 61

Tyr Leu Phe Phe Tyr Arg Lys Ser Val
 1               5

<210> SEQ ID NO 62
<211> LENGTH: 10
<212> TYPE: PRT
```

```
<213> ORGANISM: Artificial sequence
<220> FEATURE:
<223> OTHER INFORMATION: Synthetic peptide

<400> SEQUENCE: 62

Tyr Leu Gln Val Asn Ser Leu Gln Thr Val
  1               5                  10

<210> SEQ ID NO 63
<211> LENGTH: 13
<212> TYPE: PRT
<213> ORGANISM: Artificial sequence
<220> FEATURE:
<223> OTHER INFORMATION: Synthetic peptide

<400> SEQUENCE: 63

Thr Pro Pro Ala Tyr Arg Pro Pro Asn Ala Pro Ile Leu
  1               5                  10

<210> SEQ ID NO 64
<211> LENGTH: 10
<212> TYPE: PRT
<213> ORGANISM: Artificial sequence
<220> FEATURE:
<223> OTHER INFORMATION: Synthetic peptide

<400> SEQUENCE: 64

Tyr Leu Val Pro Gln Gln Gly Phe Phe Cys
  1               5                  10

<210> SEQ ID NO 65
<211> LENGTH: 9
<212> TYPE: PRT
<213> ORGANISM: Artificial sequence
<220> FEATURE:
<223> OTHER INFORMATION: Synthetic peptide

<400> SEQUENCE: 65

Arg Leu Leu Gln Glu Thr Glu Leu Val
  1               5

<210> SEQ ID NO 66
<211> LENGTH: 9
<212> TYPE: PRT
<213> ORGANISM: Artificial sequence
<220> FEATURE:
<223> OTHER INFORMATION: Synthetic peptide

<400> SEQUENCE: 66

Tyr Leu Ile His His Asn Thr His Leu
  1               5

<210> SEQ ID NO 67
<211> LENGTH: 9
<212> TYPE: PRT
<213> ORGANISM: Artificial sequence
<220> FEATURE:
<223> OTHER INFORMATION: Synthetic peptide

<400> SEQUENCE: 67

Tyr Leu Glu Glu Ile Thr Gly Tyr Leu
  1               5

<210> SEQ ID NO 68
<211> LENGTH: 9
<212> TYPE: PRT
<213> ORGANISM: Artificial sequence
```

-continued

```
<220> FEATURE:
<223> OTHER INFORMATION: Synthetic peptide

<400> SEQUENCE: 68

Tyr Leu Gln Pro Glu Gln Leu Gln Val
 1               5

<210> SEQ ID NO 69
<211> LENGTH: 9
<212> TYPE: PRT
<213> ORGANISM: Artificial sequence
<220> FEATURE:
<223> OTHER INFORMATION: Synthetic peptide

<400> SEQUENCE: 69

Tyr Leu Thr Ser Ile Ile Ser Ala Val
 1               5

<210> SEQ ID NO 70
<211> LENGTH: 126
<212> TYPE: PRT
<213> ORGANISM: Artificial sequence
<220> FEATURE:
<223> OTHER INFORMATION: Synthetic peptide

<400> SEQUENCE: 70

Val Met Ala Gly Val Gly Ser Pro Tyr Val Gln Leu Met Pro Tyr Gly
 1               5                  10                  15

Cys Leu Leu Lys Ile Phe Gly Ser Leu Ala Phe Leu Tyr Leu Val Pro
                20                  25                  30

Gln Gln Gly Phe Phe Cys Cys Leu Thr Ser Thr Val Gln Leu Val His
            35                  40                  45

Leu Tyr Gln Gly Cys Gln Val Val Ala Leu Cys Arg Trp Gly Leu Leu
        50                  55                  60

Leu Arg Leu Leu Gln Glu Thr Glu Leu Val Tyr Leu Ile His His Asn
65                  70                  75                  80

Thr His Leu Tyr Leu Glu Glu Ile Thr Gly Tyr Leu Tyr Leu Gln Pro
                85                  90                  95

Glu Gln Leu Gln Val Tyr Leu Thr Ser Ile Ile Ser Ala Val Gly Lys
            100                 105                 110

Pro Ile Pro Asn Pro Leu Leu Gly Leu Asp Ser Thr Ser Thr
        115                 120                 125
```

METHOD FOR SCREENING PEPTIDES FOR USE IN IMMUNOTHERAPY

FIELD OF THE INVENTION

Peptide vaccination or immunotherapy is a therapeutic approach which is currently the subject of a great deal of interest in the context of the prevention or treatment of viral or cancer-related pathologies. The principle thereof is based on immunization with peptides which reproduce T epitopes of viral or tumor antigens recognized by cytotoxic T cells (CTLs), in general of the CD8+ type, which play a major role in the elimination of cells expressing these antigens at their surface.

It will be recalled that CTLs do not recognize whole protein antigens, but peptide fragments thereof, generally comprising 8 to 10 amino acids, presented by the class I major histocompatibility complex (MHC I) molecules expressed at the surface of various cells. The presentation of these peptides is the result of a complex process, called "antigen processing", which involves 3 main steps:
- cytosolic degradation of the antigenic proteins by a multi-enzyme complex called proteasome;
- translocation of the peptides derived from this degradation in the endoplasmic reticulum (ER) by the TAP transporters;
- association of these peptides with the 2 chains of the MHC I so as to form stable peptide/MHC I complexes which will be exported to the cell surface.

The peptide/MHC I complexes interact with the corresponding antigen receptors (TCRs) of T lymphocytes. This interaction induces the stimulation of these lymphocytes, and cell division thereof (clonal proliferation), which results in the generation of the effector lymphocytes bearing the same TCR, which will perform the elimination of the aggressor with respect to the antigens, from which the immune response was induced.

During the processing process, a peptide selection takes place, which results in a hierarchy of presentation by the MHC I at the surface of the cell. The representation of the epitopes at the cell surface will depend in particular on the stability of the antigenic protein in the cytosol, on the sites and frequency of the cleavages performed by the proteasome, on the efficiency of translocation in the ER by the TAP transporters, and especially on the ability of the peptides to attach to the various MHC I molecules and to form stable peptide/MHC I complexes.

The peptides which are preferentially presented by the MHC at the end of the processing process constitute immunodominant epitopes, which are the main participants in the CTL response to the native antigens from which they are derived. On the other hand, the peptides which are only weakly presented constitute subdominant/cryptic epitopes which participate only slightly, or not at all, in this response.

It has been proposed to use peptides corresponding to those presented by the MHC I to induce a protective response, in particular against viral or tumor antigens.

It has thus been shown that vaccines based on immunodominant peptides, generally selected on the basis of their strong affinity for MHC I molecules, make it possible to provide antiviral or antitumor protection in many experimental murine models, and more recently in humans [SCHULTZ et al., Proc. Natl. Acad. Sci. USA, 88, 991 (1991); KAST et al., Proc. Natl. Acad. Sci. USA, 88, 2283, (1991); MARCHAND et al., Int. J. Cancer, 80, 219, (1999); ROSENBERG et al., Nature Med., 4, 321, (1998)].

However, it has also recently been shown that vaccination with immunodominant peptides might, in certain cases, prove to be ineffective. Thus, in chronic infection with a virus with a high mutation rate, such as HIV or HBV, the selection pressure imposed by the natural antiviral CTL response promotes the survival of variants having mutated in the sequence of their immunodominant peptides. These variants are no longer recognized by CTLs specific for immunodominant epitopes [KLENERMAN et al., Nature, 369, 403, (1994); BERTOLETTI et al., Nature, 369, 407, (1994); MOSKOPHIDIS and ZINKERNAGEL, J. Virol., 69, 2187, (1995); BORROW et al., Nat. Med., 3, 205, (1997); GOULDER et al., Nat. Med., 3, 212, (1997)].

Also, in the case of tumors expressing, at high levels, proteins which are also expressed in normal tissues, and which constitute "self antigens", a phenomenon of tolerance can develop. This tolerance concerns mainly the immunodominant epitopes with strong affinity for MHC. Stimulation of the CTL repertoire specific for these epitopes does not therefore appear to be the best approach for obtaining an effective antitumor protection.

The use of subdominant/cryptic epitopes, with a low affinity for the MHC, has therefore been proposed. In the case of antiviral vaccination, these epitopes, which are not subjected to a selection pressure similar to that of the immunodominant epitopes, can represent useful targets for eliminating wild-type viruses and also variants thereof. In the case of antitumor vaccination, since the low affinity epitopes participate only slightly, or not at all, in establishing tolerance, the repertoire of antitumor CTLs specific for these epitopes might remain available for in vivo recruitment.

In previous studies, the inventors' team has shown [OUKKA et al., J. Immunol., 157, 3039, (1996)] that it is possible to use subdominant/cryptic peptides in antiviral vaccination. They have also observed that the effectiveness of protection induced by subdominant/cryptic epitopes is less than that obtained with vaccination using the dominant peptide, but that it can be increased by making these peptides more immunogenic through increasing their affinity for the MHC I [TOURDOT et al., J. Immunol., 159, 2391, (1997)].

The usual strategy for increasing the immunogenicity of viral or tumor epitopes consists in increasing their affinity for the MHC I and/or the stability of the peptide/MHC I complex via amino acid substitutions. Specifically, it has been observed that the peptides capable of forming a complex with a given MHC allele have in common the presence, at certain positions, of conserved amino acid residues. A specific anchoring motif, involving amino acids called "primary anchoring residues", has thus been defined for each allele of the MHC I. It has also been shown that residues located outside the anchoring sites (secondary anchoring residues) may exert a favorable or unfavorable effect on the affinity of the peptide for the MHC; the presence of these secondary anchoring residues makes it possible to explain the existence, within the peptides having the same anchoring motif specific for a given MHC I, of great variability in the binding affinity, and why peptides which do not have the complete primary anchoring motif may be presented by the MHC I molecules and may have a strong affinity for these molecules.

Many teams have thus succeeded in increasing the immunogenicity of peptides identified as potential viral or tumor immunogens, by increasing their affinity for the MHC I. For example, in mice, LIPFORD et al. [Vaccine, 13, 313, (1995)] have shown that substituting D with I at position 2 of the peptide on the epitope 50-57 of the E6.1 Ag of the papilloma virus, presented by the $K^b$ molecule, increases the stability of the complexes formed with the $K^b$ molecule and makes the epitope immunogenic in vivo, the CTLs induced recognizing the cells transformed by the papilloma virus. BRISTOL et al. [J. Immunol., 160, 2433, (1998)] have also shown that replacing the V residue in the C-terminal position of the epitope 4-12 of the mutated Ras p21 oncogene, with I or L, which are the position-9 anchoring amino acids specific for the $K^d$ molecule, makes it possible to induce a specific CTL response in BALB/c mice. HUDRISIER et al. [Mol. Immunol., 32, 895, (1995)] have identified the residues of the peptide SMIENLEYM (SEQ ID NO: 1) which are involved in binding to the $D^b$ molecule, and have produced a series of high affinity peptides derived from the sequence $X^1AIX^4NAEAL$ (SEQ ID NO: 2) in which $X^1$=Y or K and $X^4$=E or K.

In humans, POGUE et al. [Proc. Natl. Acad. Sci. USA, 92, 8166, (1995)] have substituted amino acids at the various positions of the epitope 767-484 of the HIV-1 virus reverse transcriptase, presented by the HLA A2.1 molecule, and have shown that substitution of the residue at position 1 with Y or F increases the affinity of the peptide and its ability to induce CTLs from PBLs of seropositive donors possessing the HLA A2.1 allele. PARKHURST et al. [J. Immunol., 157, 2539, (1996)] have performed single substitutions at positions 1, 2 or 3, or double substitutions at positions 1 and 2, or 2 and 3, in the epitopes gp100 209, gp100 280 and gp100 154 of the gp100 Ag associated with melanoma, and have shown that the modified epitopes gp100 209 2M and gp100 280 9V have greater affinity than the unmodified epitope. BAKKER et al. [Int. J. Cancer, 70, 302, (1997)] have obtained, by substitution at one of the anchoring positions (position 2) or outside the anchoring positions (position 8), variants of epitope gp100 154 which have greater affinity than the native epitope. SAROBE et al. [J. Clin. Invest., 102, 1239, (1998)] have obtained an immunogenic variant of the epitope C7A of the HCV virus core protein, presented by HLA A2.1. VALMORI et al. [J. Immunol., 160, 1750, (1998)] have obtained a high affinity derivative of the epitope 26-35 of the MART-1 melanoma antigen presented by HLA A2.1.

It therefore appears to be possible to increase the immunogenicity of subdominant/cryptic epitopes in order to use them in immunotherapy. However, this requires the prior identification of these epitopes. Now, this identification remains problematic, precisely because of their poor immunogenicity.

With the aim of remedying this problem, the inventors have investigated whether it is possible to define general rules for amino acid substitution which would make it possible to increase the affinity and therefore the immunogenicity of the majority of tumor epitopes presented by the MHC (by class I HLA molecules and in particular the HLA A2.1 molecule), regardless of whether they possess the anchoring amino acids specific for this molecule and, in general, independently of their sequence of origin.

The inventors have thus noted that merely substituting the N-terminal amino acid with a tyrosine residue increases, whatever the sequence of the native peptide, the affinity of this peptide for class I HLA molecules, and in particular the HLA A2.1 molecule, and the stability of the peptide/MHC I complex formed, in a proportion which is all the greater, the lower the affinity of the native peptide. They have also observed that the peptides modified in this way keep the antigen specificity of the natural peptides, and become immunogenic and capable of recruiting, in vivo, a CTL repertoire specific for the corresponding native peptide.

A subject of the present invention is a method for identifying subdominant/cryptic epitopes presented by a class I HLA molecule, for example HLA A2.1, characterized in that it comprises at least the following steps:

a) choosing, from the sequence of a protein against which it is desired to induce a cytotoxic T response, at least one peptide sequence of 8 to 11 amino acids, capable of constituting an epitope of said protein presented by a class I HLA molecule, for example HLA A2.1, and corresponding to a peptide which has a low affinity for said class I HLA molecule and which is nonimmunogenic;

b) preparing, for each sequence selected, a variant peptide derived from said sequence by substitution of the N-terminal amino acid with a tyrosine residue;

c) determining the immunogenicity of each variant peptide obtained in step b) by selecting, from these variant peptides, each immunogenic peptide generating a specific CTL response against target cells expressing the protein from which it is derived, and identifying the peptide sequence from which said immunogenic peptide derives.

In the context of the explanation of the present invention, the term "immunogenic peptide" is intended to mean a peptide capable of inducing a specific CTL response, and the term "nonimmunogenic peptide" is intended to mean a peptide incapable of inducing a specific CTL response.

The choice of peptide sequences capable of constituting epitopes presented by a class I HLA molecule, in particular HLA A2.1, may be made, conventionally, by analyzing the peptide sequence of the chosen protein in order to select the peptides having all or part of the primary anchoring motif for a class I HLA molecule, in particular for HLA A2.1 (L at position 2 and/or V/L in the C-terminal position). Peptides known to be immunogenic will, of course, be eliminated. Optionally, a complementary selection of the peptides whose potential ability for binding to class I HLA, in particular HLA A2.1, predicted by computer analysis, appears to be the weakest may be carried out. Algorithms which can be used for this purpose are known in themselves; by way of example, mention will be made of those described by PARKER et al. [J. Immunol., 152, 163, (1994)].

This analysis may advantageously be completed by experimentally determining the binding affinity of the peptide for class I HLA, in particular HLA A2.1, and the stability of the peptide/class I HLA complex. Nonimmunogenic peptides most commonly exhibit low affinity for class I HLA, and/or form therewith a relatively unstable complex. Methods for determining the affinity of the peptide for HLA A2.1, and the stability of the complex formed, are known in themselves. Mention will, for example, be made of those described by FIRAT et al. [Eur. J. Immunol., 29, 3112, (1999)].

The affinity of a peptide for class I HLA, in particular HLA A2.1, is most commonly defined relative to that of a reference peptide, in the form of relative affinity. The relative affinity is defined as the ratio of the concentration of said peptide allowing formation of a certain amount of peptide/class I HLA complex, to the concentration of the reference peptide allowing the formation, under the same conditions, of the same amount of peptide/class I HLA complex. In this case, the higher the relative affinity, the lower the binding affinity of the peptide for class I HLA.

By way of example, for a peptide/HLA A2.1 complex, taking the peptide of sequence IVGAETFYV (SEQ ID No. 3) as reference peptide, more than 84% of the nonimmunogenic peptides will frequently have a relative affinity of greater than 10.

The stability of the peptide/HLA A2.1 complex is often defined by the DC50, which represents the time required for dissociation of 50% of complexes formed. Generally, this time is less than 2 hours for nonimmunogenic peptides.

Thus, if a peptide presented by HLA A2.1 has a relative affinity (relative to HIVpol 589) of greater than 10, and a DC50 of less than 2 hours, it will very probably be nonimmunogenic.

The immunogenicity of the peptides selected in step c) may be easily verified, for example by conventional methods for determining the ability of this peptide to generate, in vivo, ex vivo or in vitro, a specific CTL response against target cells expressing the protein from which it is derived.

Once this choice has been made, the variant peptides, derived from the selected sequences by substitution of the N-terminal amino acid with a tyrosine residue, can be very easily prepared, in particular by peptide synthesis, according to conventional techniques well known in themselves to those skilled in the art.

Advantageously, before detection of the immunogenicity of these variant peptides, carried out in step c) of the method in accordance with the invention, said method comprises a preselection of said variant peptides by determining the relative affinity of the peptide for a class I HLA molecule, in particular HLA A2.1, and/or the stability of the peptide/class I HLA complex formed, and selecting the variant peptides having a relative affinity for HLA A2.1 which is less than that of the native peptides from which they are derived, and/or a DC50 of greater than 2 hours.

Each peptide which satisfies the criteria can then be tested, in order to investigate whether it can induce a CTL repertoire specific for the nonimmunogenic native peptide from which it derives, and capable in particular of causing lysis of target cells expressing the native protein from which this nonimmunogenic peptide is derived.

If this test is positive, it may be considered that this nonimmunogenic native peptide represents a subdominant/cryptic epitope, presented by HLA A2.1, of said antigen.

The use of the method above has, for example, enabled the inventors to identify novel subdominant/cryptic epitopes, presented by HLA A2.1, of the tumor antigen HER-2/neu, of the catalytic subunit of telomerase (TERT) and of the HIV-1 virus.

These subdominant/cryptic epitopes are as follows:
For HER-2/neu:
the peptide HER-2/new 650: PLTSIISAV (SEQ ID No. 4)
the peptide HER-2/new 466: ALIHHNTHL (SEQ ID No. 5)
the peptide HER-2/neu 402: TLEEITGYL (SEQ ID No. 6)
the peptide HER-2/new 391: PLQPEQLQV (SEQ ID No. 7)
For HIV-1:
the peptide gagp24-212: EMMTACQGV (SEQ ID No. 8)
the peptide pol79: LLDTGADDTV (SEQ ID No. 9)
For the catalytic subunit of telomerase (TERT):
the peptide mhp 572: RLFFYRKSV (SEQ ID No. 10)
the peptide mhp 988: DLQVNSLQTV (SEQ ID No. 11)

A subject of the present invention is also immunogenic peptide epitopes derived from subdominant/cryptic epitopes which can be identified by using the method in accordance with the invention, and in particular from the subdominant/cryptic epitopes of HER/new, of the HIV-1 virus and of the catalytic subunit of telomerase (TERT), mentioned above.

An immunogenic peptide epitope in accordance with the invention can be obtained through various modifications of the peptide sequence of the subdominant/cryptic epitope from which it derives. Very advantageously, these modifications comprise at least the substitution of the N-terminal amino acid with a tyrosine residue. It may in particular be a variant peptide selected at the end of step c) of the method in accordance with the invention, or optionally any derivative thereof comprising other sequence modifications making it possible to increase its immunogenicity.

A subject of the present invention is also compositions comprising at least one immunogenic peptide epitope in accordance with the invention.

The immunogenic peptide epitopes in accordance with the invention can be used in all immunotherapy treatments for which it is desirable to induce a CTL response directed against subdominant/cryptic epitopes, and in particular in the context of antiviral or antitumor therapy.

Advantageously, they are multiepitope compositions which are capable of generating a polyspecific CTL response and which, for this purpose, also comprise one or more other immunogenic epitope(s). This (these) may be one or more other subdominant/cryptic epitope(s) and/or one or more immunodominant epitope(s). These epitopes may be derived from the same antigen, or from two or more different antigens.

Advantageously, multiepitope compositions in accordance with the invention may also comprise at least one epitope presented by a MHC II molecule, and capable of inducing a helper T response. They may also comprise, in order for it to be possible to use them more widely on a population in which the individuals bear different HLA alleles, one or more epitopes presented by MHC I molecules other than HLA A2.

According to a preferred embodiment of a composition in accordance with the invention, it comprises at least one chimeric polypeptide comprising one or more copies of an immunogenic peptide epitope in accordance with the invention. In the case of a multiepitope composition, said chimeric polypeptide also comprises one or more copies of at least one other immunogenic epitope.

Such a chimeric polypeptide can be easily obtained by methods known in themselves, and in particular by conventional recombinant DNA techniques.

A subject of the present invention is also a nucleic acid molecule encoding a chimeric polypeptide in accordance with the invention.

A subject of the present invention is also the use of an immunogenic peptide epitope, of a composition or of a nucleic acid molecule in accordance with the invention, for producing a medicinal product, and in particular a medicinal product intended for antiviral or antitumor immunotherapy.

The present invention also encompasses the medicinal products comprising, as active principle, at least one immunogenic peptide epitope, one composition or one nucleic acid molecule in accordance with the invention.

According to a preferred embodiment of the present invention, said medicinal products are vaccines.

Medicinal products in accordance with the invention may also comprise the usual excipients, and also adjuvants conventionally used in immunotherapy, and making it possible, for example, to promote the administration of the active principle, to stabilize it, to increase its immunogenicity, etc.

BRIEF DESCRIPTION OF THE DRAWINGS

FIG. 11B is a graph illustrating percent survival as a function of the number of days after implantation of the tumor cells.

Figure 1:
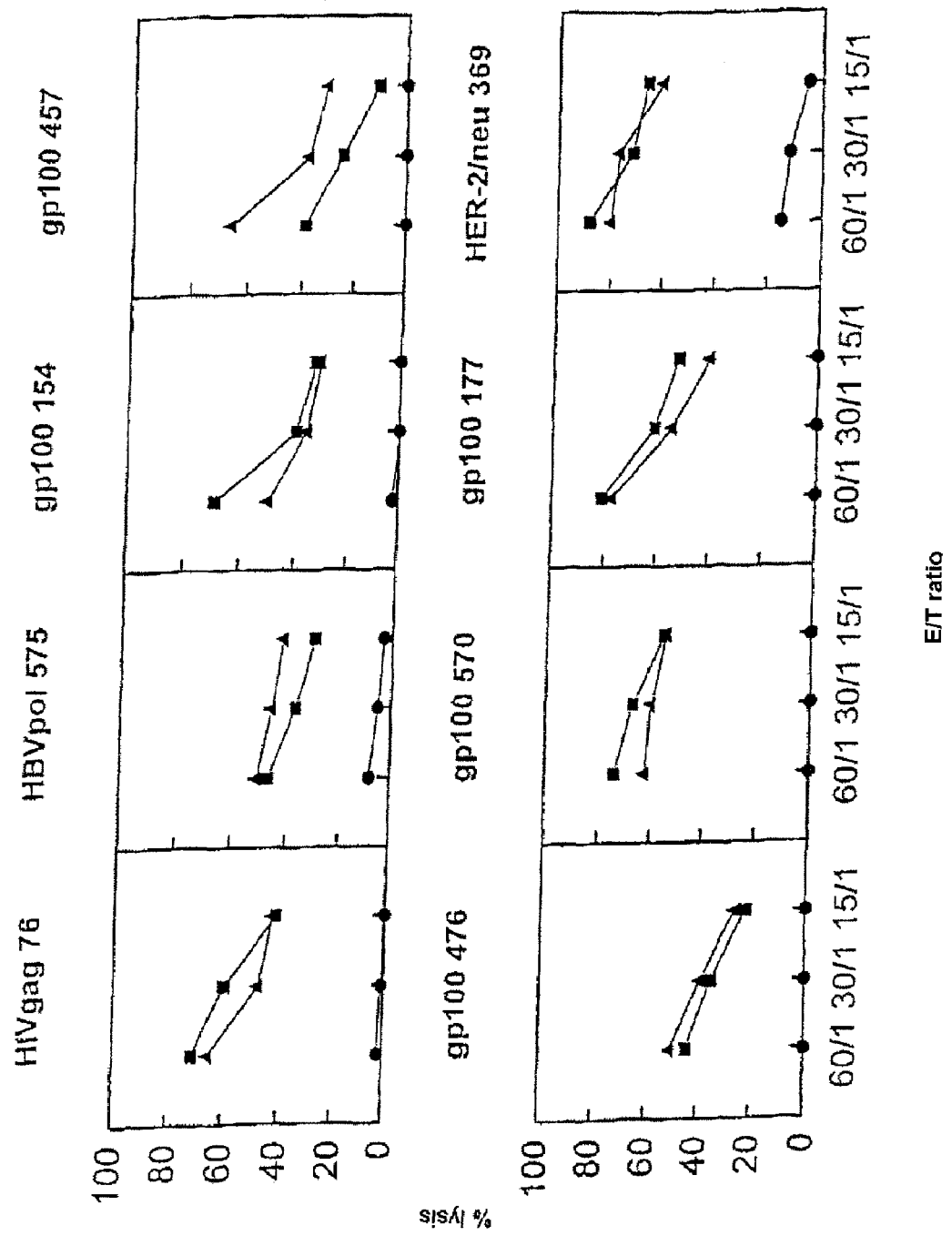
FIGS. 1-10 and 13-16 are graphs illustrating results (% lysis as a function of the effector cell/target cell ratio) obtained with various different peptides.

The present invention will be more clearly understood from the further description which follows, which refers to nonlimiting examples of identification of novel peptides and of novel antigens which can potentially be used in immunotherapy, by implementing the method in accordance with the invention.

EXAMPLE 1

Relationship Between the Affinity, the Stability of the HLA A2.1/Peptide Complexes and the Immunogenicity of the Viral and Tumor Peptides Thirty five peptides originating from viral antigens (HBV, HIV, Flu) and tumor antigens (HER-2/neu, melanoma gp100, Tyrosinase, Mart-1) were tested for their ability to attach to and to stabilize the HLA A2.1 molecule: these peptides are represented in table I below.

TABLE I

| Peptides | Sequences |
|---|---|
| Tyrosinase 224 | KLTGDENFTI (SEQ ID NO:12) |
| Tyrosinase 207 | FLPWHRLFLL (SEQ ID NO:13) |
| Tyrosinase 1* | MLLAVLYCL (SEQ ID NO:14) |
| gp100 154* | KTWGQYWQV (SEQ ID NO:15) |
| gp100 476* | VLYRYGSFSV (SEQ ID NO:16) |
| gp100 209* | TDQVPFSV (SEQ ID NO:17) |
| gp100 570* | SLADTNSLAV (SEQ ID NO:18) |
| gp100 177* | AMLGTHTMEV (SEQ ID NO:19) |
| gp100 178 | MLGTHTMEV (SEQ ID NO:20) |
| gp100 457* | LLDGTATLRL (SEQ ID NO:21) |
| mart-1 27* | AAGIGILTV (SEQ ID NO:22) |
| mart-1 32* | ILTVILGVL (SEQ ID NO:23) |
| HER-2/neu 789* | CLTSTVQLV (SEQ ID NO:24) |
| HER-2/neu 48 | HLYQGCQVV (SEQ ID NO:25) |
| HER-2/neu 650 | PLTSIISAV (SEQ ID NO:4) |
| HER-2/neu 466 | ALIHHNTHL (SEQ ID NO:5) |
| HER-2/neu 402 | TLEEITGYL (SEQ ID NO:6) |
| HER-2/neu 661 | ILLVVVLGV (SEQ ID NO:26) |
| HER-2/neu 799* | QLMPYGCLL (SEQ ID NO:27) |
| HER-2/neu 369* | KIFGSLAFL (SEQ ID NO:28) |
| HER-2/neu 851* | VLVKSPNHV (SEQ ID NO:29) |
| HER-2/neu 5* | ALCRWGLLL (SEQ ID NO:30) |
| HER-2/neu 391 | PLQPEQLQV (SEQ ID NO:7) |
| HER-2/neu 773* | VMAGVGSPYV (SEQ ID NO:31) |
| HER-2/neu 971* | ELVSEFSRM (SEQ ID NO:32) |
| HER-2/neu 1023* | YLVPQQGFFC (SEQ ID NO:64) |
| HER-2/neu 689* | RLLQETELV (SEQ ID NO:65) |
| HBVpol 985 | NLQSLTNLL (SEQ ID NO:33) |
| HBVpol 765 | LLGCAANWIL (SEQ ID NO:34) |
| HBVpol 28 | LLDDEAGPL (SEQ ID NO:35) |
| HBV pol 575* | FLLSLGIHL (SEQ ID NO:36) |
| H BVpol 594 | PLEEELPRL (SEQ ID NO:37) |
| FluM 58* | GILGFVFTL (SEQ ID NO:38) |
| HIVgag 76* | SLYNTVATL (SEQ ID NO:39) |
| HIVrt 309* | ILKEPVHGV (SEQ ID NO:40) |

Twenty two of these peptides (identified by an asterisk in table I) are already known as epitopes presented by HLA A2.1 and generating a cytotoxic CTL response in humans; the other 13 peptides, which have not yet been described as epitopes, were chosen as a function of two criteria: the presence of primary anchoring motifs of HLA A2.1 (L at position 2 and V/L in the C-terminal position) and a low binding score, according to an evaluation performed by the BIMAS program [PARKER et al., J. Immunol., 152, 163, (1994)].

The affinity for HLA A2.1 and the stability of the peptide/HLA A2.1 complex were evaluated by flow cytometry, and the immunogenicity was evaluated by generation of CTLs on HHD transgenic mice [PASCOLO et al., J. Exp. Med., 185, 2043, (1997)].

The protocols used are as follows [FIRAT et al., Eur. J. Immunol., 29, 3112, (1999)]:

Affinity:

Human T2 cells [FIRAT et al., Eur. J. Immunol., 29, 3112, (1999)] ($3\times10^5$ cells/ml), which are deficient in TAP transporters, are incubated at 37° C. for 16 hours with various concentrations of each peptide to be tested, in serum-free RPMI 1640 medium supplemented with 100 ng/ml of human β2-microglobulin. Next, they are washed twice and labeled with the monoclonal antibody BB7.2 [PARHAM et al., Hum. Immunol., 3, 4, 277-299, (1981)] which is specific for the HLA A2.1 molecule, and then with an anti-mouse Ig goat antibody coupled to fluorescein isothiocyanate (FITC).

The cells are then analyzed by flow cytometry. For each concentration of peptide, the HLA A2.1-specific fluorescence is calculated as a percentage of the fluorescence obtained with 100 μM of a reference peptide (HIVpol 589; IVGAETFYV (SEQ ID No. 3)). The relative affinity (RA) is defined as the ratio of the concentration of each peptide which induces 20% of the fluorescence obtained with 100 μM of the reference peptide, to the concentration of the reference peptide which induces 20% of the fluorescence obtained with 100 μM of said reference peptide. The lower the relative affinity, the stronger the binding of the peptide to HLA A2.1. The mean RA for each peptide is determined from at least three independent experiments. In all the experiments, 20% of the maximum fluorescence was obtained for 1 to 3 μM of the reference peptide.

Stability:

T2 cells ($10^6$/ml) are incubated overnight at 37° C. with 100 μM of each peptide to be tested, in serum-free RPMI 1640 medium supplemented with 100 ng/ml of human β2-microglobulin. Next, the cells are washed four times to remove the free peptides, incubated with Brefeldin A (SIGMA; 10 μg/ml) for one hour to prevent expression at their surface of newly synthesized HLA A2.1 molecules, washed and incubated at 37° C. for 0, 2, 4, 6 or 8 hours. For each incubation time, the cells are then labeled, as indicated above, with the BB7.2 antibody, and analyzed by flow cytometry in order to evaluate the amount of peptide/HLA A2.1 complex present at their surface. This amount is evaluated by the formula: (mean fluorescence of T2 cells preincubated with the peptide— mean fluorescence of T2 cells treated under similar conditions in the absence of peptide). The DC50 (dissociation complex: DC) is defined as being the time required for the loss of 50% of the HLA A2.1/peptide complexes stabilized at t=0.

Immunogenicity:

The HHD mice used are β2m−/−, $D^b$−/−, and express a single-chain HLA A2.1 composed of the α1 and α2 domains of HLA A2.1 and of the α3 and intracellular domains of $D^b$ linked via its N-terminal to the C-terminal of human β2-m by a 15 amino acid peptide.

The mice are given a subcutaneous injection, at the base of the tail, of 100 μg of each peptide to be tested, emulsified in incomplete Freund's adjuvant, in the presence of 140 μg of a helper T epitope derived from the "core" antigen of HBV (128-140, sequence TPPAYRPPNAPIL (SEQ ID No. 63)).

After 11 days, spleen cells taken from the mice (5×10⁷ cells in 10 ml) are stimulated in vitro with the peptide to be tested (10 μM). On the 6th day of culture, the populations which respond are tested in order to determine specific cytotoxicity. In certain cases, the cells which respond are restimulated in vitro at one-week intervals with 2×10⁶ irradiated (3 000 rads) HHD spleen cells and 10 μM of peptide in the presence of 20 IU/ml of recombinant IL2.

RMA-HHD and RMAS-HHD cells are used as targets to study the cytotoxicity. These cells are respectively obtained by transfecting murine RMA cells and their TAP-deficient variant RMAS cells with the HHD construct as described by PASCOLO et al. [J. Exp. Med., 185, 2043, (1997)]. They are infected with viruses expressing the various antigens from which the peptides to be tested are derived.

The viruses used are as follows: the recombinant vaccinia virus expressing HIVgag VVTG1144 (vac-HIVgag) described by JOHNSON [J. Immunol., 147, 1512, (1991)]; the recombinant vaccinia virus expressing HER-2/neu VT39 (vac-neu) (Therion Biologics); the vaccinia virus vac-gp100, described by YANG [J. Immunol., 164, 4204, (2000)]; a wild-type vaccinia virus (vac-WT); and the flu PR8 virus for influenza described by VIRELIZIER [J. Immunol., 115, 2, 434-439, (1975)]. For the viral infections, the RMA-HHD cells are incubated for 16 hours with the recombinant or wild-type vaccinia viruses (10 PFU/cell), or with the flu PR8 virus (50 HAU) for 2 hours.

The target cells are labeled with 150 μCi of $^{51}$Cr for 90 minutes, then washed three times and plated out into round-bottomed 96-well plates (10⁴ cells/well in 100 μl of RPMI 1640+3% of fetal calf serum).

Noninfected RMA-HHD or RMAS-HHD cells are loaded with 1 μM of peptide to be tested, at 37° C. for 90 minutes.

Next, 100 μl of the effector cells, at various concentrations, are added to the wells, and the plates are incubated at 37° C. for 4 hours. After incubation, 100 μl of supernatant are collected and the radioactivity is measured in a γ-counter.

The percentage specific lysis is calculated using the formula: [(experimental release of $^{51}$Cr-spontaneous release of $^{51}$Cr)/(maximum release of $^{51}$Cr-spontaneous release of $^{51}$Cr)]×100. In all the experiments, the spontaneous release is less than 20% of the maximum release induced with 3N HCl.

The 34 peptides were classified into three different groups as a function of their ability to attach to and to stabilize the HLA A2.1 molecule, and of their immunogenicity; the results of this classification are given in table II.

TABLE II

| Peptides | RA | DC50 (hours) | Responders*/total mice |
|---|---|---|---|
| Group I | | | |
| HIV gag 76 | 1.0 | >8 | 7/10 |
| Flu M58 | 0.2 | >8 | 4/6 |
| HBV pol 575 | 2.6 | >8 | 6/8 |
| HBV pol 765 | 2.0 | 4 | ND |
| Mart-1 27 | 2.2 | 2-4 | 4/5 |
| gp100 177 | 0.5 | >6 | 3/5 |
| gp 100 178 | 0.3 | 6-8 | 4/6 |
| gp 100 154 | 2.3 | 6-8 | 7/9 |
| gp 100 570 | 1.0 | 4-6 | 6/9 |
| gp100 209 | 1.3 | 4 | 4/6 |
| gp100 476 | 10.0 | 6 | 8/10 |
| gp 100 457 | 1.6 | 2-4 | 4/6 |
| HER-2/neu 799 | 1.0 | 6-8 | 3/4 |
| HER-2/neu 369 | 2.3 | 4 | 12/13 |
| HER-2/neu 789 | 1.6 | 6-8 | 4/6 |
| HER-2/neu 48 | 1.7 | >8 | 5/6 |
| HER-2/neu 773 | 1.7 | 6 | 2/3 |
| HER-2/neu 5 | 2.3 | >8 | 5/6 |
| HER-2/neu 689 | 2 | 4 | 5/6 |
| Group II | | | |
| Tyrosinase 1 | >60.0 | 2-4 | 4/23 |
| Mart-1 32 | 21.1 | 4 | 0/10 |
| HER-2/neu 851 | 24.0 | 4 | 1/12 |
| HER-2/neu 661 | >60.0 | 2-4 | 0/6 |
| HER-2/neu 1023 | 19.6 | 4 | 5/10 |
| Group III | | | |
| HBV pol 28 | 5.3 | <2 | 0/6 |
| HBV pol 594 | 4.2 | <2 | 0/6 |
| HBV pol 985 | 43.3 | <2 | 0/6 |
| Tyrosinase 224 | >50.0 | <2 | 0/6 |
| Tyrosinase 207 | >50.0 | 2 | 0/6 |
| HER-2/neu 650 | 1.4 | <2 | 0/6 |
| HER-2/neu 466 | 4.8 | 2 | 0/6 |
| HER-2/neu 402 | 19.0 | <2 | 0/6 |
| HER-2/neu 391 | >70.0 | 2 | 0/6 |
| HER-2/neu 971 | >70.0 | 2 | 0/6 |

*It is considered that the mice respond when a specific cytotoxicity against targets pulsed with a peptide is greater than 15% of the toxicity against the unloaded targets.

It is considered that the mice respond when a specific cytotoxicity against targets pulsed with a peptide is greater than 15% of the toxicity against the unloaded targets.

The first group consists of 19 peptides having an RA≦10 and a DC50>2 hours. They correspond to antigenic epitopes of viruses or of tumors (with the exception of HBVpol 765 and HER-2/neu 48) and trigger a CTL response in a high percentage (60 to 92%) of the HHD mice.

The second group of five peptides with an RA>10 and a DC 50>2 hours comprises three known epitopes, and a potential epitope (HER-2/neu 661). Two of them are nonimmunogenic (Mart-1 32, HER-2/neu 661), while HER-2/neu 851 and tyrosinase 1 induce a response in a low percentage of HHD mice (8% and 17%, respectively).

Ten peptides with a DC50<2 hours and a variable RA belong to the third group. They do not correspond to known epitopes (with the exception of HER-2/neu 971) and they are nonimmunogenic in HHD mice, even if they have a high RA such as HBVpol 28, HBVpol 594, HER-2/neu 650 and HER-2/neu 466.

The following conclusions can be drawn from these results: (i) secondary anchoring motifs greatly influence HLA A2.1 binding since peptides having the optimal HLA A2.1 primary anchoring residues exhibit a very broad spectrum of affinities, (ii) the binding affinity does not always correlate with the ability to stabilize the HLA A2.1 molecule. The Mart-1 32 and HER-2/neu 851 peptides are weak binders but they form stable peptide/HLA A2.1 complexes. On the contrary, the HBVpol 28, HBVpol 594, HER-2/neu 650 and HER-2/neu 466 peptides are powerful binders but they form unstable complexes with the HLA A2.1 molecule, (iii) the immunogenicity of the peptides depends mainly on their ability to stabilize the HLA A2.1 molecule. Peptides having a DC50<2 hours are never immunogenic even if they have a strong binding affinity. However, HLA A2.1 stability induced by a peptide is not sufficient to ensure immunogenicity. Specifically, peptides having a DC50>2 hours may be nonimmunogenic (Mart-1 32 and HER-2/neu 661) or very weakly immunogenic (Tyrosinase 1 and HER-2/neu 851) if they exhibit a low binding affinity.

It therefore appears that it is necessary to improve both the binding affinity and the ability to stabilize the HLA A2.1 molecule in order for peptides to generate a strong CTL response.

EXAMPLE 2

Effect of Replacing the Residue at Position P1 with a Tyrosine on the Affinity and the Stability of the HLA A2.1/Peptide Complex Variants of 33 peptides described in example 1, resulting from substitution of the 1st N-terminal amino acid with a tyrosine (substitution P1Y), were synthesized. These variants were tested for their affinity for the HLA A2.1 molecule and their ability to stabilize the complex formed.

The results are given in table III.

TABLE III

| Peptide | RA WT/RA Y1 | DC50 Y1-DC50 WT |
|---------|-------------|-----------------|
| HIV gag 76 | ↑3.0 | =0 |
| Flu M58 | ↑2.4 | =0 |
| H BV pol 575 | ↑2.6 | =0 |
| HBV pol 765 | ↑40.4 | ↑4 |
| Mart-127 | ↑2 | =0 |
| gp100 177 | =0.6 | ↑2 |
| gp100 178 | =0.8 | ↑2 |
| gp100 154 | =0.8 | ↓2 |
| gp100 570 | ↑3.4 | ↑>2 |
| gp100 209 | =1.7 | ↑2 |
| gp100 476 | ↑4.2 | ↑2 |
| gp 100 457 | ↑2.3 | ↑>2 |
| HER-2/neu 369 | ↑3.9 | ↑>2 |
| HER-2/neu 799 | ↑3.9 | ↑>2 |
| HER-2/neu 789 | ↑2.1 | =0 |
| HER-2/neu 48 | ↑3.0 | =0 |
| HER-2/neu 773 | ↑2.0 | ↑2 |
| HER-2/neu 5 | =1.1 | =0 |
| HER-2/neu 689 | ↑3.1 | ↑>2 |
| Tyrosinase 1 | ↑>3.7 | ↑>2 |
| Mart-1 32 | ↑16.2 | ↑2 |
| HER-2/neu 851 | ↑3.0 | ↑2 |
| HER-2/neu 661 | ↑>1.5 | ↑2 |
| HBV pol 28 | ↑2.3 | ↑>2 |
| HBV pol 594 | ↑14.8 | ↑>6 |
| H BV pol 985 | ↑13.7 | ↑>6 |
| Tyrosinase 224 | ↑>5.1 | ↑>2 |
| Tyrosinase 207 | ↑>6.4 | ↑>4 |
| HER-2/neu 650 | ↑6.0 | ↑>4 |
| HER-2/neu 466 | ↑3.3 | ↑>4 |
| HER-2/neu 402 | ↑5.2 | ↑>2 |
| HER-2/neu 391 | ↑55.5 | ↑>6 |
| HER-2/neu 971 | ↑11.6 | ↑2 |

These results show that the substitution P1Y increases the binding of all the low affinity peptides, and promotes HLA A2.1 stabilization for all the weakly stabilizing peptides (groups II and III in table II). The increase in affinity, measured by the ratio between the RAs of the modified peptide and of the natural peptide, is a minimum of 1.5 and ranges up to 55.5, while the increase in HLA A2.1 stabilization, measured by the difference between the DC50s of the modified peptide and of the natural peptide, is a minimum of 2 hours and ranges up to 6 hours. The RA of all the modified peptides, with the exception of one of them (HER-2/neu 661Y1) is less than 10, and their DC50 is >4 hours. For the Tyrosinase 1 and HER-2/neu 661 peptides, the modification P1Y does not generate any peptide having a very strong affinity. This is due to the presence in these peptides of P3-P8/9 secondary anchoring residues which are unfavorable for HLA A2.1 binding.

The effect of the substitution P1Y is not limited to the low affinity peptides, but is also observed with the majority of the high affinity peptides (group I of table II). Only two of the nineteen high affinity peptides showed no improvement in either their binding affinity or their stabilizing ability (gp100 154 and HER-2/neu 5). It should be noted that an increase in affinity is independent of the nature of the residue at position 1 of the native peptide and that it is observed even if the residue substituted is not a residue unfavorable to binding with HLA A2.1. Only four of the 19 peptides having a natural peptide RA/modified peptide RA ratio greater than 3 have an unfavorable residue at P1 (P for HER-2/neu 391, HER-2/neu 650 and HBVpol 594, E for HER-2/neu 971). The increase in affinity of these four peptides is, however, very large: it is between 6 and 55.5.

However, the affinity is increased even when Y substitutes another favorable residue such as F (HBVpol 575 and Tyrosinase 207).

These results demonstrate that a substitution P1Y increases the binding to HLA A2.1 and the ability to stabilize the complex formed for almost all the peptides bound to HLA A2.1. This effect is much more pronounced for the nonimmunogenic peptides with a low affinity for HLA A2.1.

EXAMPLE 3

Cross-Recognition of the Natural Peptides and of Their P1Y Variants by Specific CTLs The increase in affinity for HLA A2.1 is the first condition for making low affinity peptides immunogenic. It is, however, also necessary for their conformation in the complex with HLA A2.1 not to be modified, and for their antigenic specificity to be conserved. If such is the case, CTLs generated in HHD mice vaccinated with the native peptide should recognize this native peptide and its P1Y variant with the same efficacy. In addition, the P1Y variants should be capable of recruiting, in vivo, the repertoire of CTLs specific for the natural peptide.

Recognition of the P1Y variants by natural peptide-specific CTLs was first of all studied. CTLs induced in HHD mice sensitized with the HIVgag 76, HBVpol 575, gp100 154, gp100 457, gp100 476, gp100 570, gp100 177 or HER-2/neu 369 peptides were tested for their ability to kill RMAS-HHD targets loaded with either the natural peptides (WT) or the corresponding P1Y variants (P1Y).

FIG. 1 illustrates the results (% lysis as a function of the effector cell/target cell ratio) obtained with eight different peptides.
RMAS-HHD cells loaded with the natural peptide: ■
RMAS-HHD cells loaded with the P1Y peptide: ▲
Unloaded RMAS-HHD cells: ●.

These results show that CTLs induced in HHD mice sensitized with the HIVgag 76, HBVpol 575, gp100 154, gp100 457, gp100 476, gp100 570, gp100 177 and HER-2/neu 369 peptides kill the RMAS-HHD cells loaded with the natural peptide or with its P1Y variant with the same efficacy.

The P1Y variants are also capable of recruiting the CTLs specific for the natural peptide in vivo. Spleen cells from HHD mice sensitized with the P1Y variants HIVgag 76Y1, HBVpol 575Y1, gp100 154Y1, gp100 457Y1; gp100 476Y1, gp100 570Y1, gp100 177Y1 and HER-2/neu 369Y1 were tested for their ability to kill RMAS-HHD targets loaded with either the P1Y variants (P1Y) or with the wild-type peptides (WT).

Figure 2:
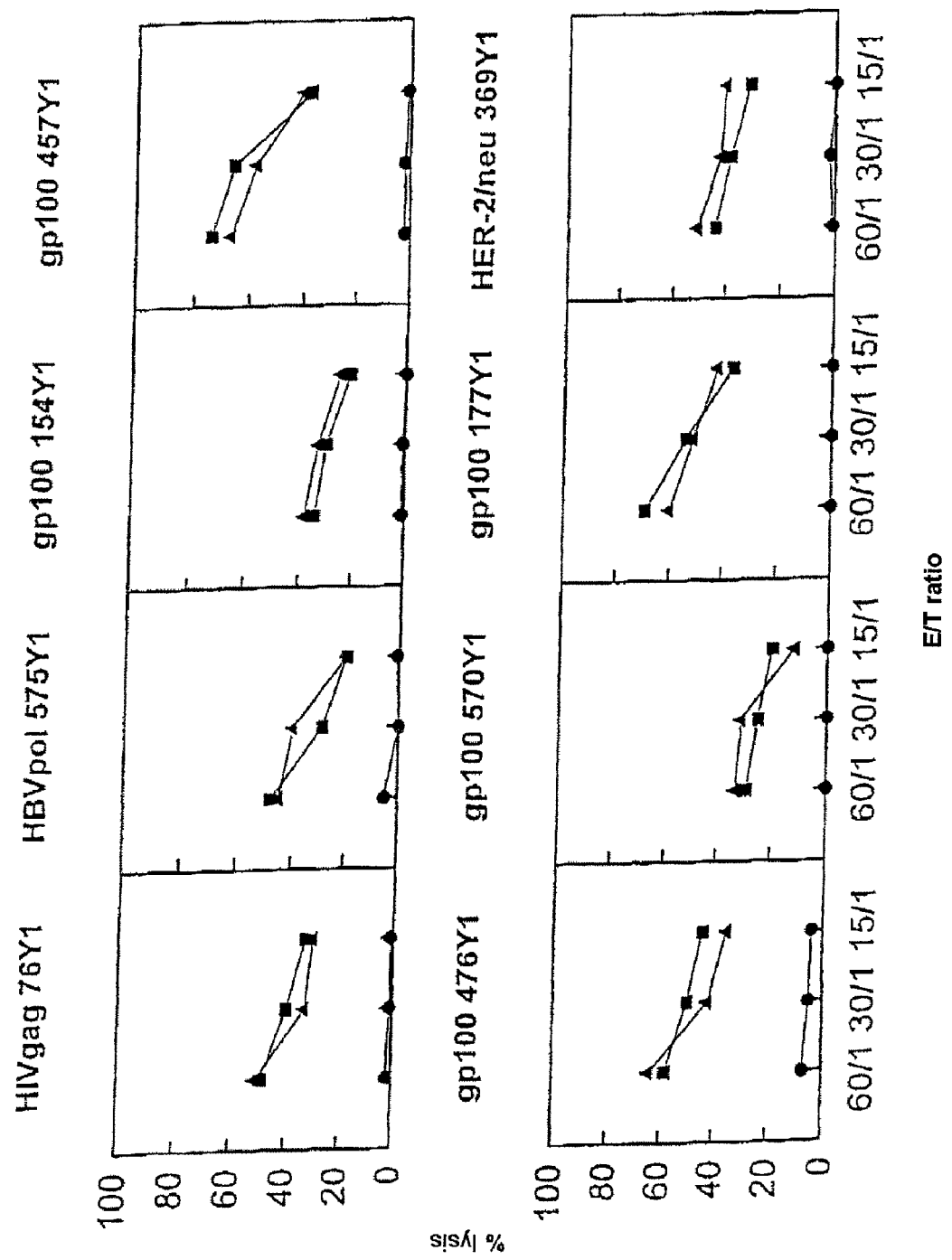

The results (% lysis as a function of the effector cell/target cell ratio) are given in FIG. 2.
RMAS-HHD cells loaded with the natural peptide: ■
RMAS-HHD cells loaded with the P1Y peptide: ▲

Unloaded RMAS-HHD cells: ●.

These results show that the P1Y variants generate CTLs which kill the RMAS-HHD targets loaded with the variant peptide or with the corresponding natural peptide.

In addition, all these variant peptides, with the exception of gp100 154Y1, induce CTLs in a higher percentage of HHD mice than do the corresponding natural peptides. Three to eight HHD mice were tested for each peptide, and a CTL response was induced in 100% of the mice sensitized with HIVgag 76Y1, HBVpol 575Y1, gp100 476Y1, gp100 570Y1 and HER-2/neu 369Y1, and in 75% of the mice sensitized with gp100 457Y1, gp100 177Y1 and gp100 154Y1.

In addition, the CTLs induced by the P1Y variants recognize these variants and the corresponding natural peptides with comparable avidities.

The CTLs generated in mice sensitized with the P1Y variants HER-2/neu 369Y1, HIVgag 76Y1 and gp100 154Y1 were tested for their ability to kill RMAS-HHD targets loaded with various concentrations of the P1Y variant peptide, or of the corresponding wild-type peptide.

Figure 3:
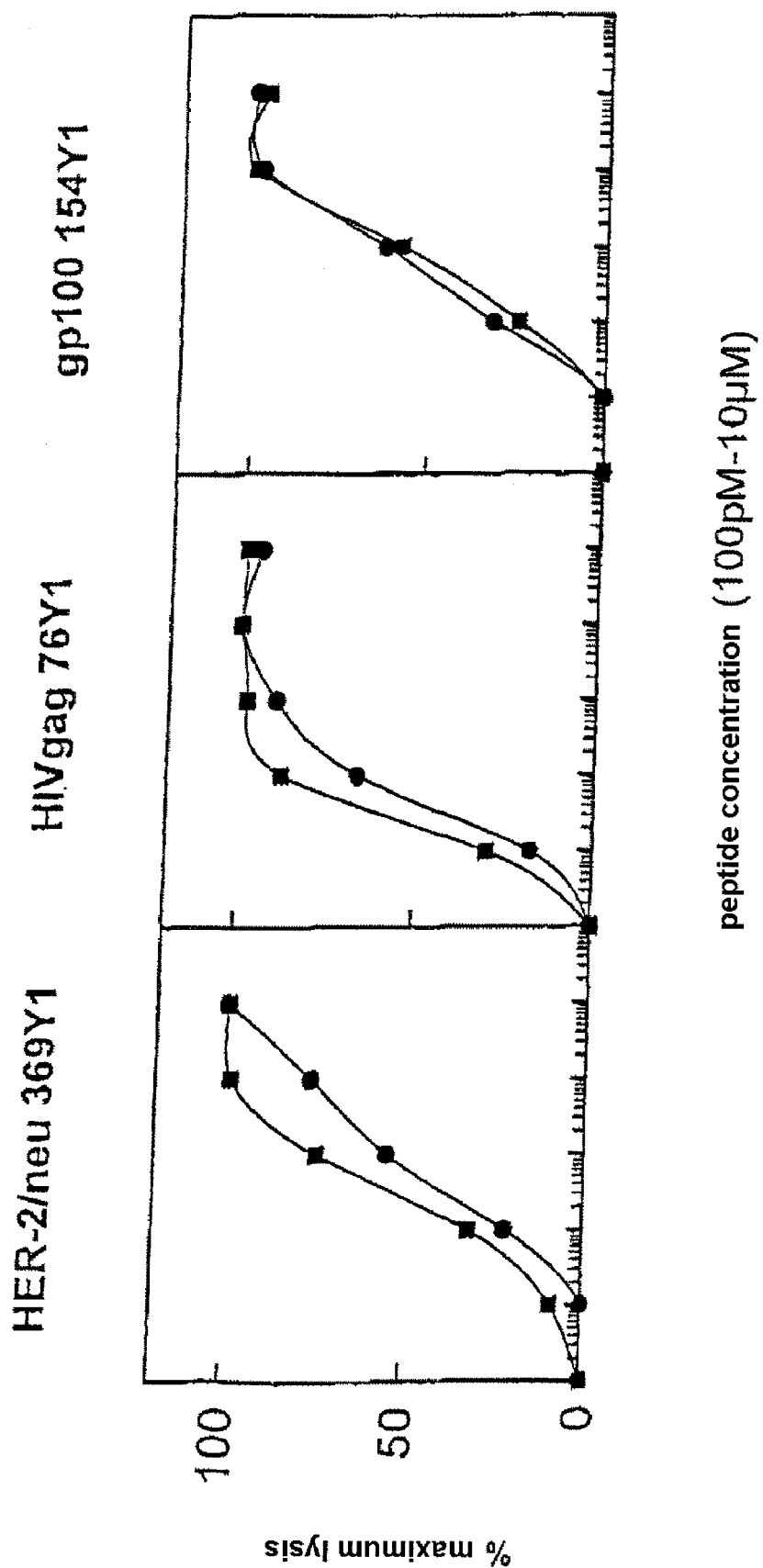

The results (% lysis as a function of the effector cell/target cell ratio) are given in FIG. 3.
RMAS-HHD cells loaded with the natural peptide: ●
RMAS-HHD cells loaded with the P1Y peptide: ■.

These results show that the CTLs induced by the P1Y variants give a cytolysis equal to half the maximum cytolysis for similar amounts of P1Y variant and of natural peptide.

In order to envisage using the P1Y variants in immunotherapy, it is also necessary for the CTLs induced by these variants to recognize naturally processed epitopes of the antigen from which they are derived.

CTLs generated in mice sensitized with HIVgag 76Y1, HER-2/neu 369Y1, HER-2/neu 5Y1, gp100 476Y1 and fluM 58Y1 were tested in order to determine their ability to kill RMA-HHD cells infected with the recombinant viruses vac-HIVgag, vac-neu, vac-gp100 or flu PR8, and endogenously expressing the corresponding viral antigens, or infected with the wild-type virus vac-WT.

Figure 4:
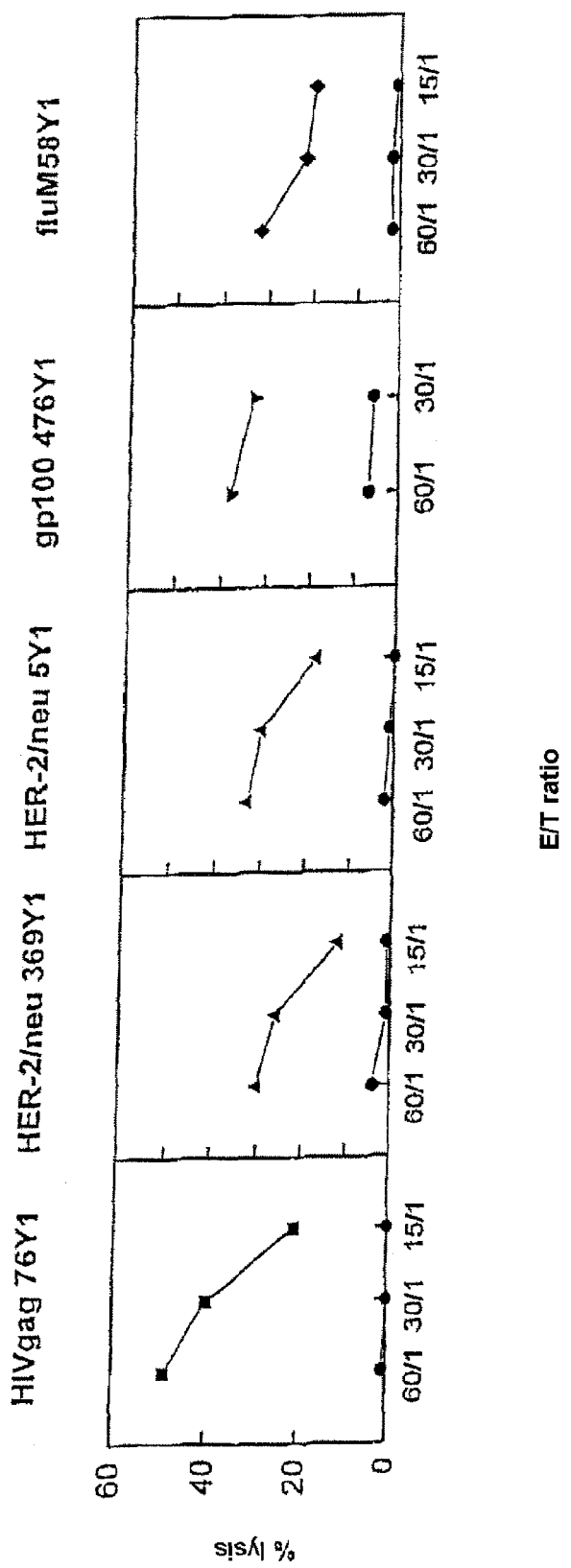

The results (% lysis as a function of the effector cell/target cell ratio) are given in FIG. 4:
RMA-HHD cells infected with vac-WT (●);
RMA-HHD cells infected with vac-HIVgag (■);
RMA-HHD cells infected with vac-neu (▲);
RMA-HHD cells infected with vac-gp100 (▼);
RMA-HHD cells infected with flu PR8 (◆).

These results show that CTLs specific for the P1Y variants recognize the naturally matured epitope since they kill targets infected with the corresponding virus but not the targets infected with vac-wt.

It appears therefore that the P1Y substitution satisfies the two criteria which are necessary for induction of a CTL response against any peptide with a low affinity for HLA A2.1, whatever its sequence. First, it increases the binding affinity and the stabilizing ability of the peptides bound to HLA A2.1 and, second, it does not interfere with the peptide/TCR interaction and does not therefore modify their antigenic specificity.

EXAMPLE 4

Restoration of the Immunogenicity of Nonimmunogenic Peptides with a Low Affinity for HLA A2.1, with a P1Y Substitution Mice were vaccinated with P1Y variants of the HER-2/neu 402, HER-2/neu 466, HER-2/neu 650, HER-2/neu 391, Tyrosinase 207, HBVpol 594, HBVpol 28 and HBVpol 985 peptides. Eleven days later, their spleen cells are restimulated in vitro with the corresponding natural peptide, and the CTLs generated are tested against RMAS-HHD target cells which are unloaded or loaded with the natural peptide.

Figure 5:
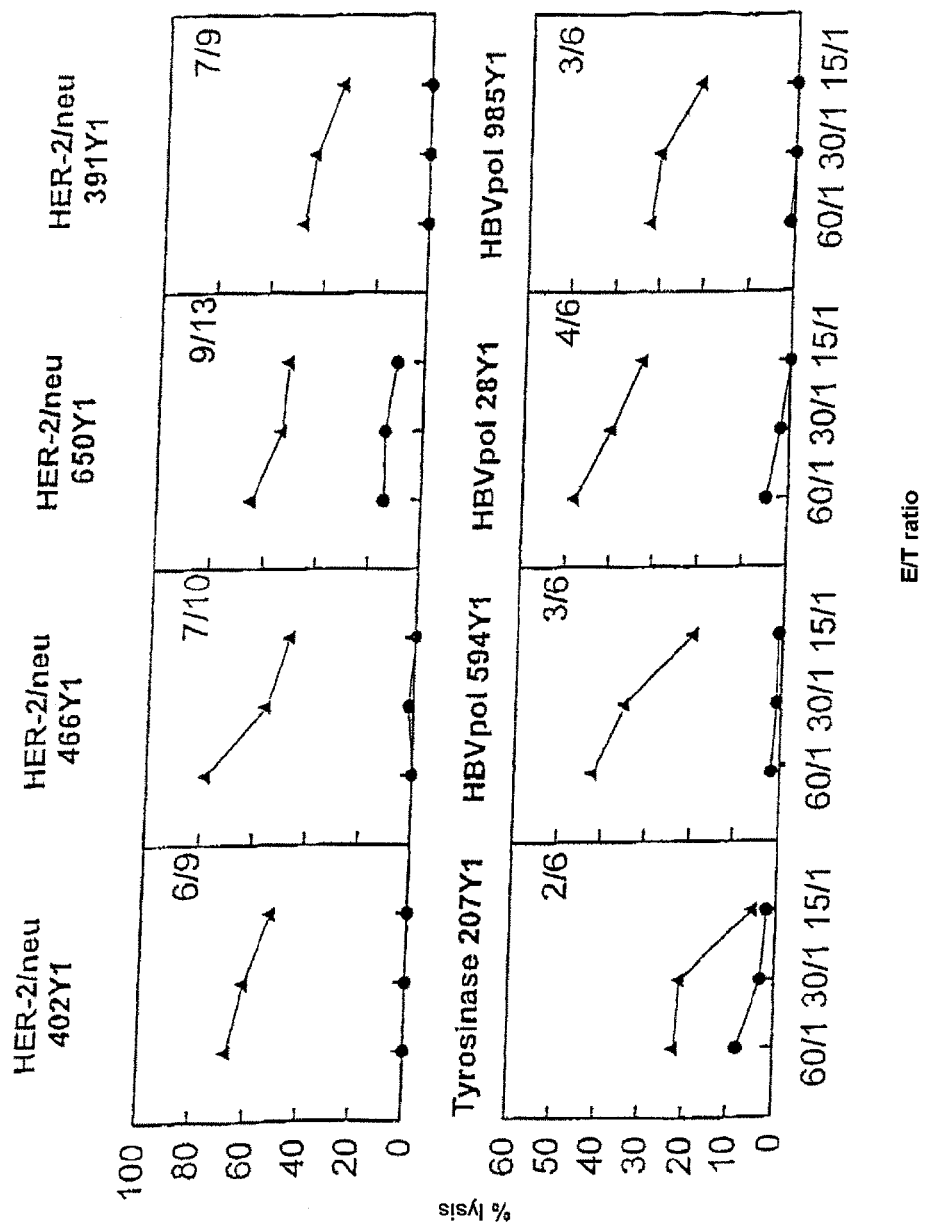

The results (% lysis as a function of the effector cell/target cell ratio) are given in FIG. 5:
RMAS-HHD cells loaded with the natural peptide: ▲
Unloaded RMAS-HHD cells: ●.

For each peptide, the number of mice which respond is indicated.

These results show that the HHD mice sensitized with P1Y variants generate CTLs specific for the natural peptide. In addition, the percentage of mice which give a response is relatively high: it is between 33 and 77%.

These data demonstrate that a P1Y substitution constitutes a general strategy for increasing the immunogenicity of non-immunogenic peptides with a low affinity for HLA A2.1.

EXAMPLE 5

Identification of Subdominant/Cryptic Epitopes Using P1Y Variants

The possibility of inducing a CTL response against peptides with a low affinity for HLA A2.1 makes it possible to identify viral or tumor subdominant/cryptic epitopes which are of use for specific immunotherapy.

This possibility is illustrated below using the example of 3 different antigens: the tumor antigen HER-2/neu, the HIV-1 virus and the catalytic subunit of telomerase (hTERT).

HER-2/neu Epitopes:

The HER-2/neu 650 peptide does not contribute to the HER-2/neu-specific CTL response developed in patients bearing a HER-2/neu+ tumor. Two hypotheses are possible: either it is an epitope which is not naturally matured by tumor cells expressing HER-2/neu, or it is a subdominant/cryptic epitope.

As described in example 1 above, the HER-2/neu 650 peptide forms unstable HLA A2.1/peptide complexes and is not therefore immunogenic.

1) In order to study whether the HER-2/neu 650 peptide corresponds to a subdominant/cryptic epitope, the CTLs generated in mice sensitized with the variant HER-2/neu 650Y1 are tested for their ability to kill RMA-HHD cells infected with vac-neu.

Figure 6:
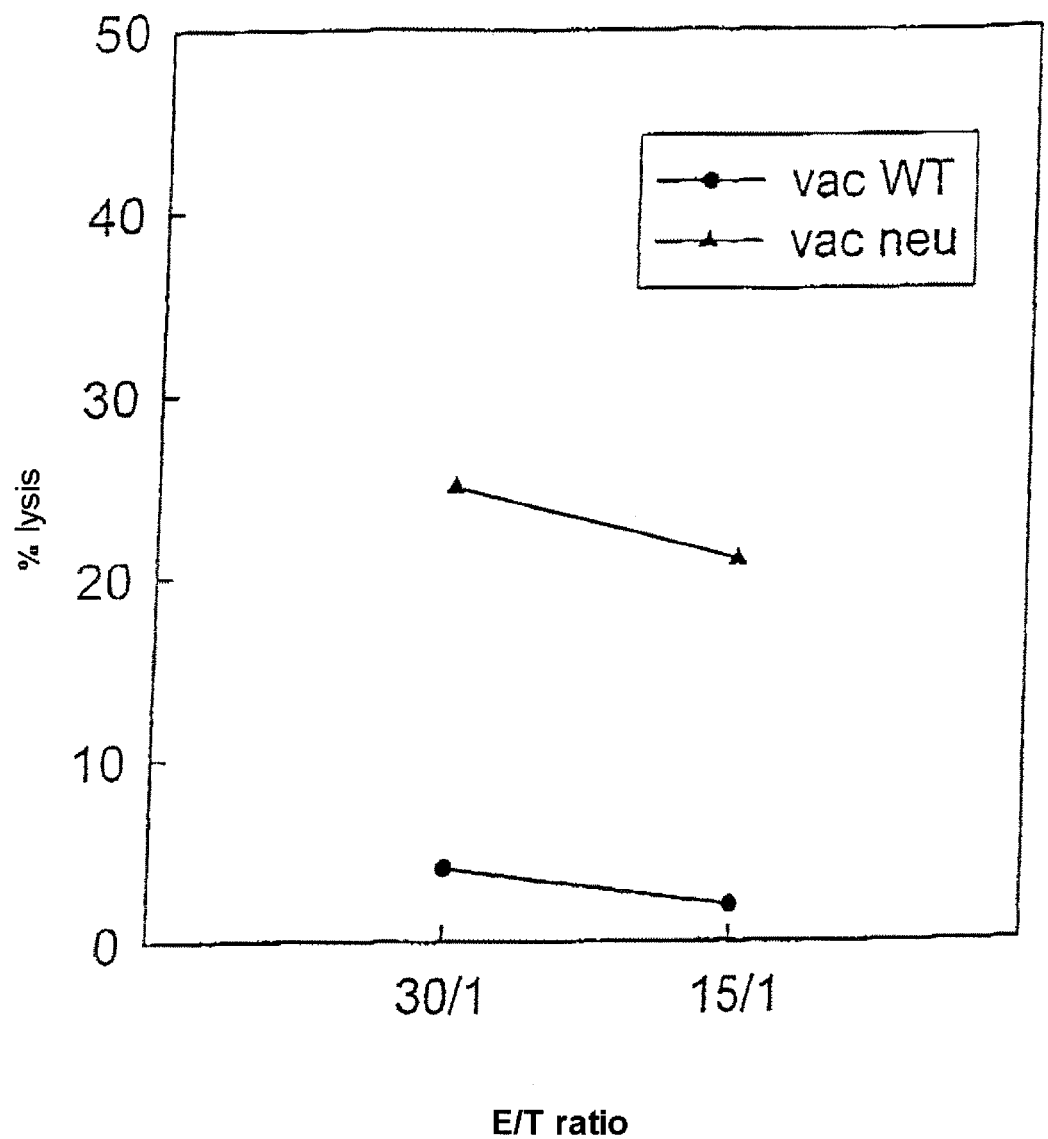

The results (% lysis as a function of the effector cell/target cell ratio) are given in FIG. 6:
RMA-HHD cells infected with vac-WT (●)
RMA-HHD cells infected with vac-neu (▲).

These results show that HER-2/neu 650-specific CTLs kill target cells infected with vac-neu, but not targets infected with vac-WT, which demonstrates that the HER-2/neu 650 peptide is a subdominant/cryptic epitope of HER-2/neu.

The P1Y variants of the HER-2/neu 466, HER-2/neu 402, HER-2/neu 661 and HER-2/neu 391 peptides were tested in the same way; with the exception of the P1Y variant of HER-2/neu 661, the results are similar to those observed for HER-2/neu 650.

The HER-2/neu 466, HER-2/neu 402 and HER-2/neu 391 peptides therefore also constitute subdominant/cryptic epitopes of HER-2/neu.

As regards HER-2/neu 661, the results obtained confirm those relating to the small increase in affinity described in example 2 above. Additional modifications will have to be carried out in order to envision using this peptide in immunotherapy.

2) The immunogenicity of the variants HER-2/neu 466Y1, HER-2/new 402Y1, HER-2/neu 650Y1, and HER-2/neu 391Y1 in accordance with the invention, relative to an immunodominant peptide, was also evaluated on human cells, and compared to that of the immunodominant peptide HER-2/neu 369.

Peripheral blood mononuclear cells (PBMCs) were obtained from HLA A2.1 healthy donors and resuspended in 2 ml of RPMI 1640 culture medium supplemented with 10 nM of glutamine, 250 units/ml of penicillin-streptomycin, and 10% of heat-inactivated human AB serum, and incubated at 37° C. for 2 hours. The nonadherent cells are collected, and the remaining adherent cells are loaded with the peptide to be tested (5 µM), at 37° C. for 90 minutes, and irradiated at 3 000 rads; they are then washed in order to remove the free peptide.

$3 \times 10^6$ nonadherent cells are added to a final volume of 2 ml of culture medium supplemented with 50 IU/ml of recombinant IL-2. On the seventh day, they are harvested, washed, and suspended in culture medium, and restimulated with $5 \times 10^6$ adherent autologous cells preloaded with the peptide to be tested as described above. The following day, 150 IU/ml of recombinant IL-2 are added. On the ninth or the tenth day, the cultures are supplemented with 300 IU/ml of recombinant IL-2. When necessary, the medium is changed by removing 1 ml of culture supernatant and replacing it with 1 ml of culture medium containing 300 IU/ml of recombinant IL-2. This procedure is repeated at least 3 times at one-week intervals.

T2 cells loaded with the native peptide (1 µM of peptide, 37° C., 90 minutes) corresponding to the P1Y peptide to be tested are used as targets to study the cytotoxicity.

Figure 7:
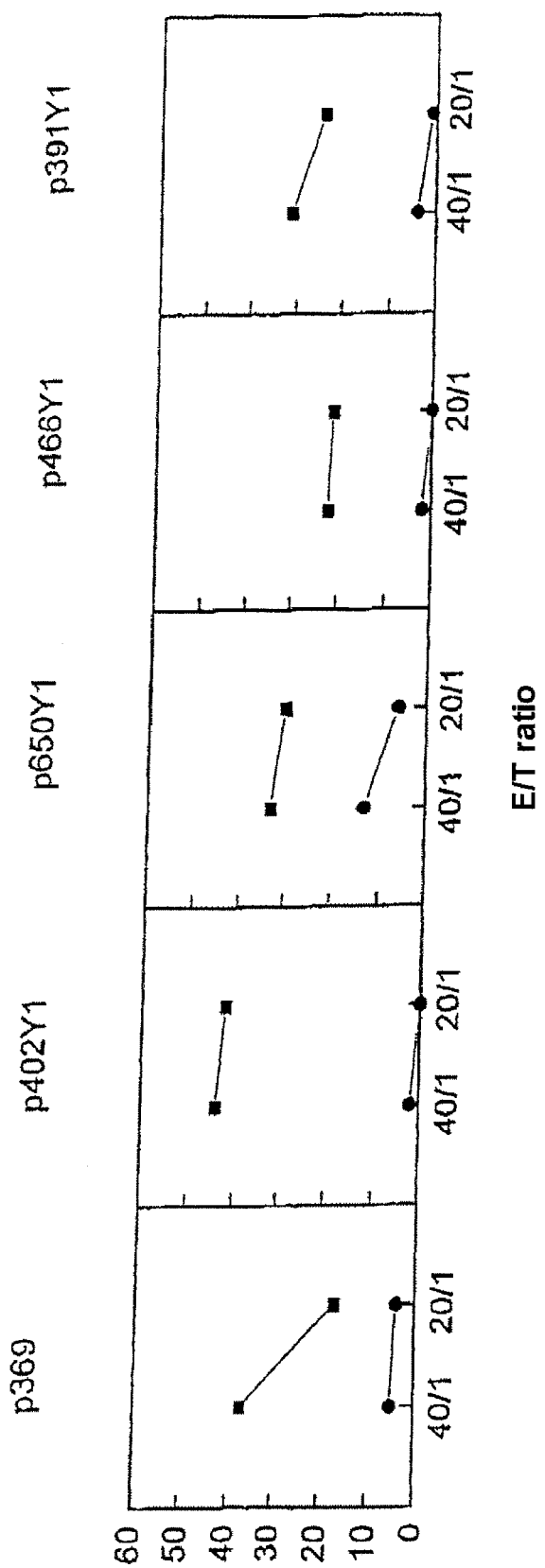

The results (% lysis as a function of the effector cell/target cell ratio) for each of the peptides tested are given in FIG. 7:
T2 cells loaded with the natural peptide: ■
Unloaded T2 cells ●.

These results show that the P1Y substitution also increases the immunogenicity with respect to human cells.

3) In order to verify whether the P1Y peptides induced human CTLs specific for naturally processed tumor epitopes, CTLs generated, as described above, from human PBMCs, originating from 3 different donors, stimulated with HER-2/neu 369, or with the HER-2/neu 466 Y1, HER-2/neu 402, HER-2/neu 650 Y1 and HER-2/neu 391 Y1 peptides, were also tested for their ability to kill HLA A2.1+ human tumor cells expressing the HER-2/neu epitope in reasonable amounts.

The tumor cells used as target cells are as follows:
4 HLA A2.1+/HER-2/neu+ cell lines: MC F-7 [ZAKS, Cancer Res., 58, 4902, (1998)]; PUB/N (human "non small cells" lung cancer tumor line); HCT-116 [BROS-SART, Cancer Res., 58, 732, (1998)]; LAW (human kidney cancer tumor line);
2 HLA A2.1+/HER-2/neu– cell lines: ZR75.1 [OSBORNE et al., Cancer Res., 39, 2422-2428, (1979)]; SUP/M2 [MORGAN et al., Blood, 73, 8, 2155-2164, (1989)];
by way of a control, the K562 line, sensitive to lysis by NK cells.

The expression of the HER-2/neu tumor antigen by these cells, evaluated by immunofluorescence using an anti-HER-2/neu monoclonal antibody, is given in table IV below.

TABLE IV

| Cell line | HER-2/neu (FI) |
|---|---|
| ZR75.1 | 0.12 |
| SUP/M2 | 0.11 |
| MCF-7 | 1.94 |

TABLE IV-continued

| Cell line | HER-2/neu (FI) |
|---|---|
| HCT-116 | 1.23 |
| PUB/N | 1.33 |
| LAW | 0.35 |

Figure 8:
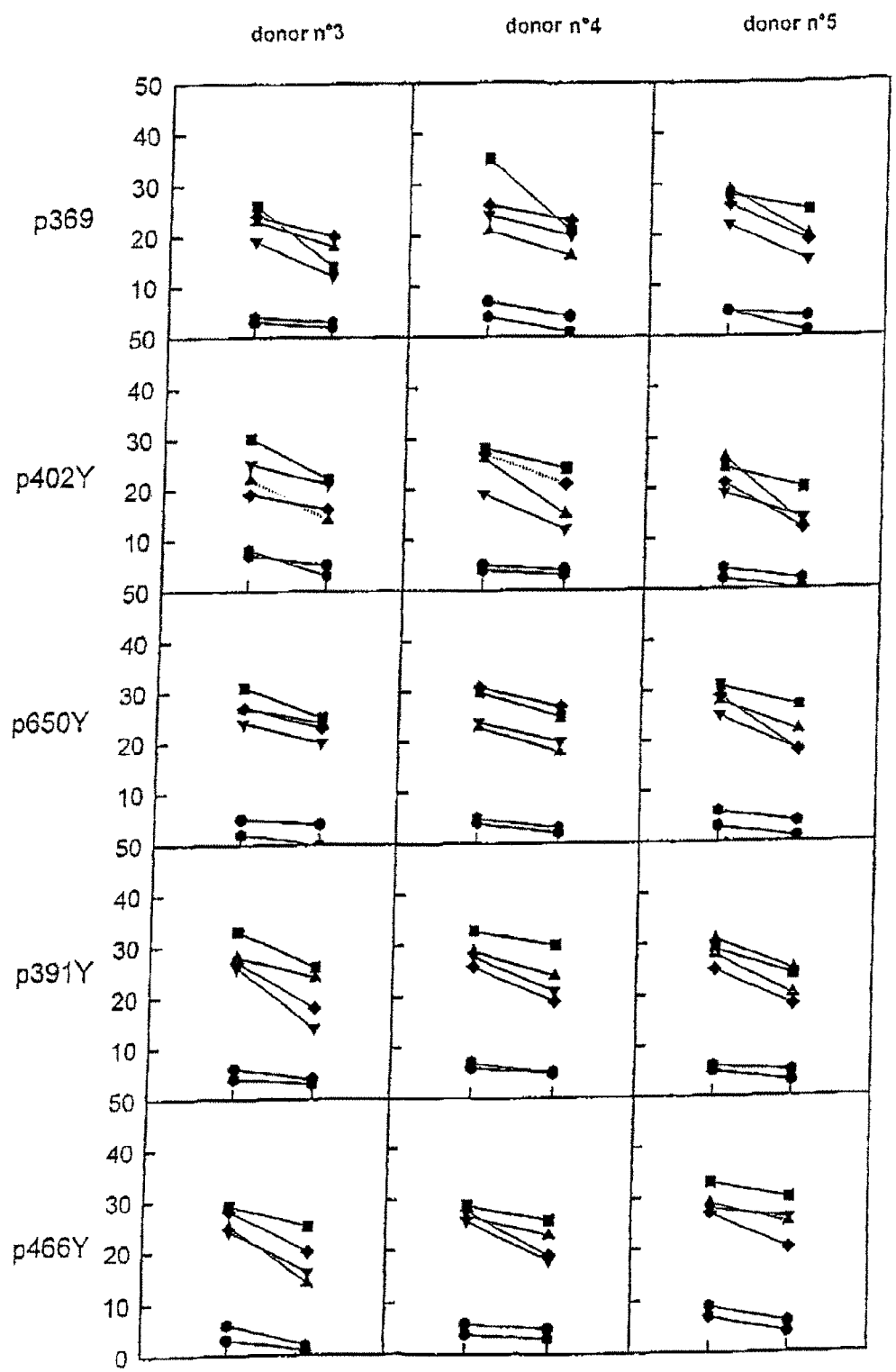

The results of these cytotoxicity assays (% lysis as a function of the effector cell/target cell ratio; E/T ratios: 40/1; 20/1) for each of the peptides tested are given in FIG. 8:
ZR75.1 cells: ●
SUP/M2 cells: ◕
MCF-7 cells: ■
HCT-116 cells: ▼
PUB/N cells: ▲
LAW: ◆.

No cytotoxicity with respect to the K562 cells is observed.

These results show that the CTLs obtained from the PBMCs of 3 different donors, stimulated with the P1Y variant peptides, lyse the HER-2/neu+ cells MCF-7, PUB/N, HCT-116 and LAW, but not the HER-2/neu– cells ZR75.1 and SUP/M2.

It should be noted that the lysis is as effective in the case of the LAW cells, which express the HER-2/neu antigen only weakly, as in that of the MCF-7, PUB/N and HCT-116 cells, which express it at a high level. This shows that the presentation of the low affinity epitopes does not require the expression of the antigen at a high level.

HIV 1 Epitopes:

The P1Y substitution was used to identify novel subdominant/cryptic epitopes of HIV 1.

17 peptides of HIV Gag, Pol, Env and Nef were chosen from the complete polypeptide sequence of HIV 1. The list of these peptides is given in table V below.

TABLE V

| Protein of origin* | | Peptides | Frequency among HIV 1 isolates (%)** |
|---|---|---|---|
| GAG | p17 (77-85) | SLYNTVATL (SEQ ID NO:39) (S9L) | 39.6 |
| | p24 (19-27) | TLNAWVKVV (SEQ ID NO:41) (T9V) | 62.5 |
| | p24 (212-221) | EMMTACQGV (SEQ ID NO:8) (E9V) | 95.8 |
| POL | (79-88) | LLDTGADDTV (SEQ ID NO:9) (L10V) | 96.8 |
| | (188-196) | ALVEICTEM (SEQ ID NO:42) (A9M) | 46.2 |
| | (263-273) | VLDVGDAYFSV (SEQ ID NO:43) (V11V) | 84.9 |
| | (334-342) | VIYQYMDDL (SEQ ID NO:44) (V9L) | 84.9 |
| | (464-472) | ILKEPVHGV (SEQ ID NO:45) (I9V) | 68.8 |
| | (576-584) | PLVKLWYQL (SEQ ID NO:46) (P9L) | 87.1 |
| | (669-679) | ESELVNQIIEQ (SEQ ID NO:47) (E11Q) | 33.3 |
| | (671-680) | ELVNQIIEQL (SEQ ID NO:48) (E10L) | 33.3 |
| | (956-964) | LLWKGEGAV (SEQ ID NO:49) (L9V) | 98.9 |
| ENV | gp120 (120-128) | KLTPLCVSL (SEQ ID NO:50) (K9L) | 8.9 |
| | gp120 (120-128) | KLTPLCVTL (SEQ ID NO:51) (K9L/T) | 79.4 |
| | gp41 (260-268) | RLRDLLLIV (SEQ ID NO:52) (R9V) | 0.3 |

TABLE V-continued

| Protein of origin* | Peptides | Frequency among HIV 1 isolates (%)** |
|---|---|---|
| NEF | (134-143) PLTFGWCFKL (SEQ ID NO:53) (P10L) | 0.1 |
|  | (188-196) AFHHVAREL (SEQ ID NO:54) (A9L) |  |

*The amino acid numbering is based on the sequence of the HIV 1 clone WEAU 1.60 (Genbank accession number U21135). This reference is simply given to indicate the location of the peptides in this table relative to the viral proteins; the sequence of these peptides is not always completely identical to that of the corresponding peptides of the WEAU clone.
**The frequency was calculated from the isolates available on the database "HIV Molecular Immunology Database".

The relative affinity of these peptides for HLA A2.1 (reference peptide I9V), and the stability of the peptide/HLA A2.1 complex were determined as described in example 1 above, for the native peptide, and for its variant resulting from substitution of the N-terminal amino acid with a tyrosine.

The results are given in table VI below:

TABLE VI

| CD8 epitope peptides |  | Native peptides | | P1Y peptides | |
|---|---|---|---|---|---|
|  |  | RA | DC | RA | DC |
| GAG | S9L | 2.2 | >6 h | 5 | >6 h |
|  | T9V | 5.5 | 3.5 h | 5.5 | >6 h |
|  | E9V | 21 | <2 h | 1.7 | >6 h |
| POL | L10V | 10 | <2 h | 1.5 | 4 h |
|  | A9M | 5 | 2 h | 1.75 | >6 h |
|  | V11V | 4.5 | 2 h | 2.5 | 3.5 h |
|  | V9L | >100 | ND | 8.6 | <2 h |
|  | I9V | 1 | 5 h | ND | ND |
|  | P9L | >100 | ND | 4.6 | <2 h |
|  | E11Q | >100 | ND | >100 | ND |
|  | E10L | >100 | ND | 10 | <2 h |
|  | L9V | 3.1 | >6 h | 1.3 | >6 h |
| ENV | K9L | 1.35 | >6 h | 0.7 | >6 h |
|  | K9L/T | 0.65 | >6 h | 0.4 | >6 h |
|  | R9V | >100 | ND | 5 | ND |
| NEF | P10L | >100 | ND | 5 | ND |
|  | A9L | >100 | ND | 7 | >6 h |

The two peptides gagp24-212 (E9V) and pol79 (L10V) have a low affinity and a weak stabilizing ability (RA>5 and DC50<2 hours); on the other hand, their P1Y variants have a high affinity and a strong stabilizing ability (RA<5 and DC50>2 hours). The immunogenicity of the E9V and L10V peptides and of their P1Y variants was also tested. The native peptides are not immunogenic; on the other hand, their variants are immunogenic both in the HHD mice and in humans.

In addition, CTLs generated from human PBMCs, originating from 6 different donors, stimulated in vitro with autologous cells loaded with the variant peptide E9VY or the variant peptide L10VY, or with the immunodominant native peptide S9L, were also tested for their ability to kill RMA-HHH cells (RMA cells expressing the native HLA A2.1 molecule) infected with a recombinant vaccinia virus expressing either the gag protein or the pol protein of HIV1 (LAI isolate), or with a control, wild-type vaccinia virus.

Figure 9:
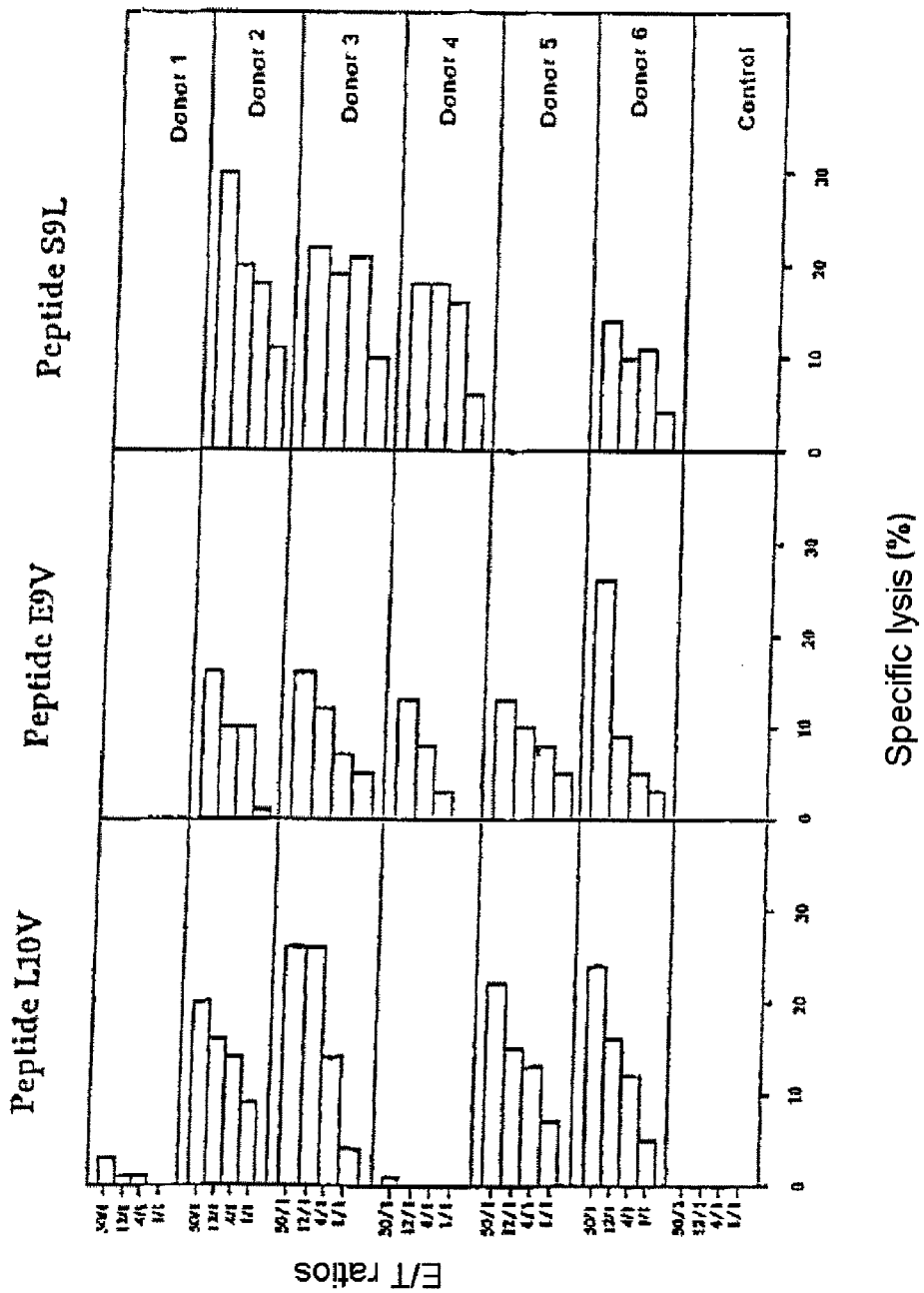

The results are given in FIG. 9 (on the X axis: % specific lysis; on the Y axis: effector cell/target cell ratio). These results show that the E9V and L10V peptides are naturally presented by cells which express HLA-A2.1 and the viral protein from which they are derived (gag for E9V and pol for L10V).

Epitopes of the Catalytic Subunit of Telomerase (hTERT):

The P1Y substitution was used to determine whether the catalytic subunit of telomerase (hTERT) possess epitopes capable of inducing a cytotoxic T response.

8 peptides were chosen from the polypeptide sequence of the catalytic subunit of telomerase (hTERT).

The relative affinity of these peptides for HLA A2.1, and the stability of the peptide/HLA A2.1 complex, were determined as described in example 1 above (reference peptide: HIVpol 589).

The results are given in table VII below:

TABLE VII

| Native peptides | Sequences | RA | DC50 |
|---|---|---|---|
| mp 530 | ILATFLAWL (SEQ ID NO:55) | 0.8 | >6 |
| mp 534 | FLFWLMDTYV (SEQ ID NO:56) | 0.2 | >6 |
| mp 545 | QLLRSFFHFL (SEQ ID NO:57) | 1.8 | >6 |
| mp 797 | SLFDFFHFL (SEQ ID NO:58) | 1.5 | >6 |
| mp 876 | FLSTLVHGV (SEQ ID NO:59) | 1.2 | >6 |
| mhp 540 | ILAKFLHWL (SEQ ID NO:60) | 0.3 | >6 |
| mhp 572 | RLFFYRKSV (SEQ ID NO:10) | 25.3 | <2 |
| mhp 988 | DLQVNSLQTV (SEQ ID NO:11) | 28.6 | <2 |

The two peptides mhp 572 and mhp 988 have a low affinity and a weak stabilizing ability (RA>5 and DC50<2 hours). These 2 peptides are also common to the catalytic subunit of human telomerase (hTERT) and to the catalytic subunit of murine telomerase (mTERT). The P1Y variants of these 2 peptides, resulting from substitution of the N-terminal amino acid with a tyrosine, were prepared, and their relative affinity for HLA A2.1, and the stability of the peptide/HLA A2.1 complex, were determined.

The results, given in table VIII below, show that these variants mhp 572Y1 and mhp 988Y1 have a high affinity and a strong stabilizing ability (RA<5 and DC50>2 hours).

TABLE VIII

| Modified peptides | Sequences | RA | DC50 |
|---|---|---|---|
| mhp 572Y1 | YLFFYRKSV (SEQ ID NO:61) | 2.2 | 5 |
| mph 988Y1 | YLQVNSLQTV (SEQ ID NO:62) | 2.1 | >6 |

CTLs generated from human PBMCs, originating from healthy donors, stimulated in vitro with autologous dendritic cells loaded with the variant peptide mhp 572Y1 or the variant peptide mhp 988Y1 were tested for their ability to kill HLA A2.1+/hTERT+ human tumor cells: U266 [VONDERHEIDE, Immunity, 10, 11, (1999)], or HSS HLA A2.1−/hTERT+ human tumor cells: [VONDERHEIDE, Immunity, 10, 11, (1999)].

Figure 10:
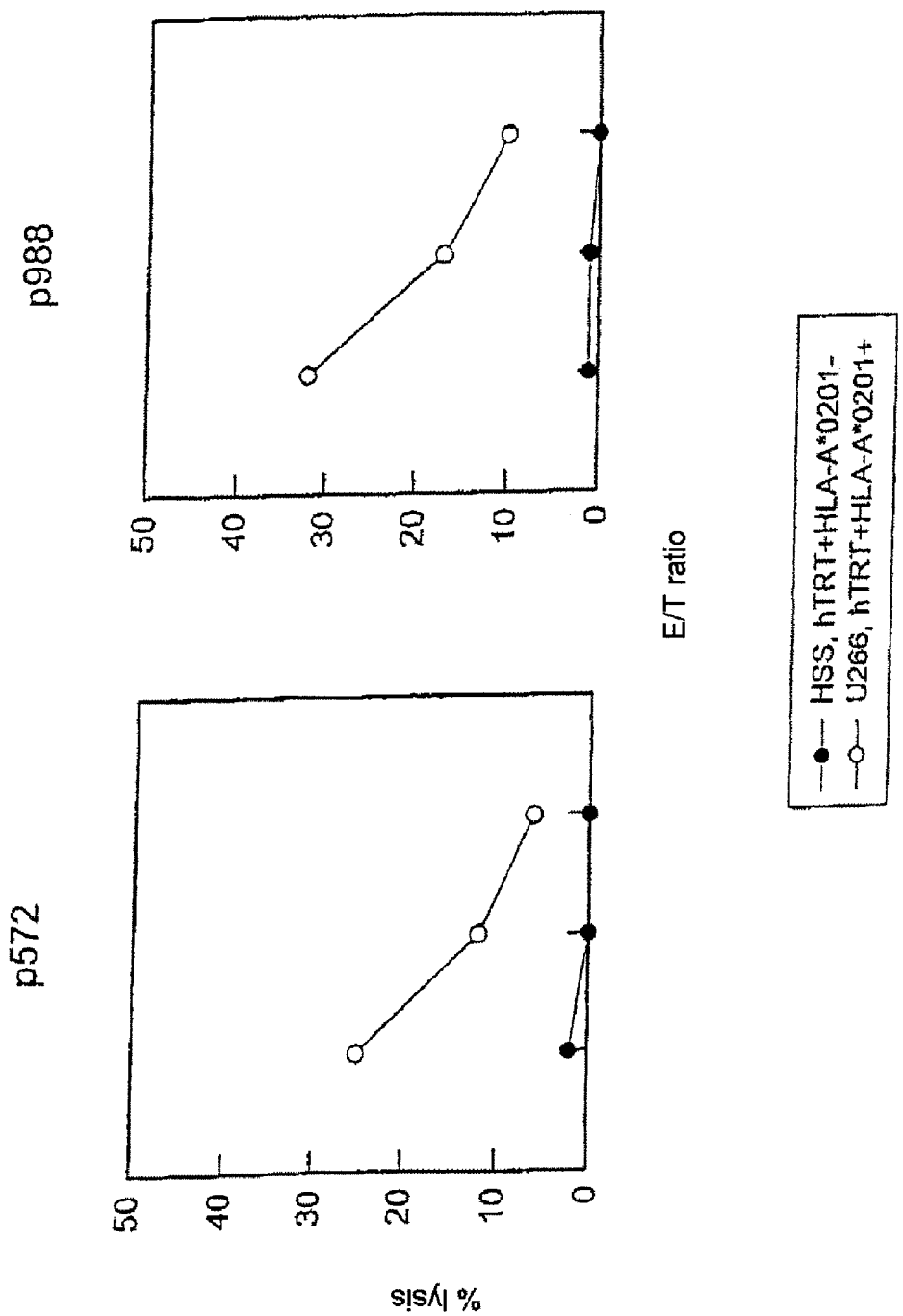

The results (% lysis as a function of the effector cell/target cell ratio; E/T ratio: 40/1; 20/1; 10/1) are given in FIG. 10: no lysis is observed for the HSS tumor cells which do not express HLA A2.1; on the other hand, considerable lysis is observed in the case of the U266 tumor cells which express both the catalytic subunit of telomerase (hTERT) and HLA A2.1.

These results show that the mhp 572 and mhp 988 peptides are naturally presented by the human tumor cells, and that immunogenic derivatives of these peptides can potentially be used in antitumor immunotherapy.

EXAMPLE 6

Antitumor Activity of the P1Y Variants

I. Derivatives of the Epitope of the Catalytic Subunit of Telomerase (hTERT)

P1Y variants (mhp 572Y1 and mhp 988Y1), obtained as described in example 2, are tested for their ability to induce, in vivo, a protective antitumor response, with immunodominant peptides (mp 797 and mp 545).

Ten HHD mice generated as described in example 1 are vaccinated, at a rate of two injections two weeks apart, with these various peptides synthesized by Synt:em (Nîmes, France).

Seven days after the final injection, EL-4/HHD cells [PAS-COLO et al., J. Exp. Med., 185, 2043-2051 (1997)] are grafted into the mice vaccinated with the mhp 572Y1, mhp 988Y1, mp 797 and mp 545 peptides.

Figure 11:
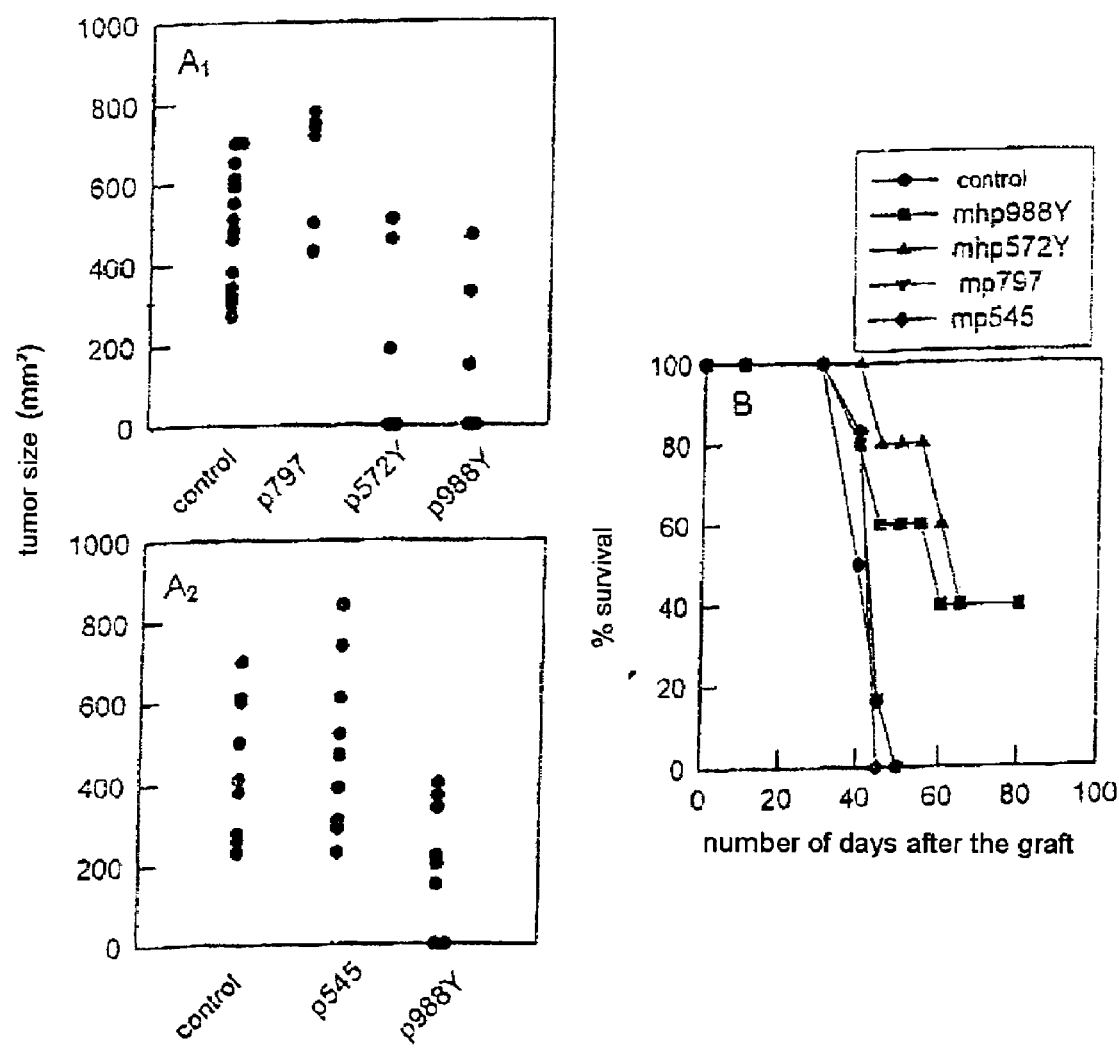
FIGS. 11$A_1$ and 11$A_2$ are graphs illustrating tumor size as a function of the peptides used.

The effectiveness of the antitumor protection is evaluated by measuring the size of the tumors 28 days after implantation thereof (FIGS. $11A_1$ and $11A_2$: tumor size as a function of the peptides used for the vaccination) and by the survival of the grafted mice (FIG. 11B: % survival as a function of the number of days after implantation of the tumor cells).

The results are given in FIGS. $11A_1$, $11A_2$ and 11B: it is observed that, at D28, the tumors measure 490±144 mm$^2$ and 653±148 mm$^2$, respectively, in the untreated (control) mice and in the mice treated with the mp 797 peptide, 421±170 mm$^2$ and 489±209 mm$^2$, respectively, in the untreated (control) mice and in the mice treated with the mp 545 peptide, but that in the batch of mice vaccinated with the mhp 572Y1 and mhp 988Y1 peptides, the tumors measure, respectively, 232±244 mm$^2$ and 190±207 mm$^2$ (FIG. $11A_1$) or 213±160 mm$^2$ (FIG. $11A_2$), and that 4 mice vaccinated with mhp 572Y1 and mhp 988Y1, respectively, show no tumors at D28.

All the unvaccinated mice die at D50 (FIG. 11B: ●).

For the mice vaccinated with the mp 797 and mp 545 peptides (FIG. 11B: ▼ and ♦), mortality is observed from D40 and the final mouse dies at D50.

The mortality is significantly reduced in the batch of mice vaccinated with mhp 572Y1 and mhp 988Y1 (FIG. 11B: ▲ and ■). It appears that D40 and 4 mice (40%) are still alive at D80 (FIG. 11B: ▲, ■).

II. Derivatives of the HER-2/neu Epitope

P1Y variants (HER-2/neu 650Y1, HER-2/neu 402Y1), obtained as described in example 2, are tested for their ability to induce, in vivo, a protective antitumor response, with immunodominant peptides (HER-2/neu 369, HER-2/neu 48).

Ten HHD mice generated as in example 1 are vaccinated, at a rate of two injections two weeks apart, with these various peptides synthesized by Synt:em (Nîmes, France).

HER-2/HHD/neu cells are obtained by transfecting EL-4/HHD tumor cells with the cDNA encoding the HER-2/neu molecule.

Seven days after the final injection, EL-4/HHD/neu tumor cells are grafted into the mice vaccinated with the HER-2/neu 650Y1, HER-2/neu 402Y1, HER-2/neu 369 and HER-2/neu 48 peptides.

Figure 12:
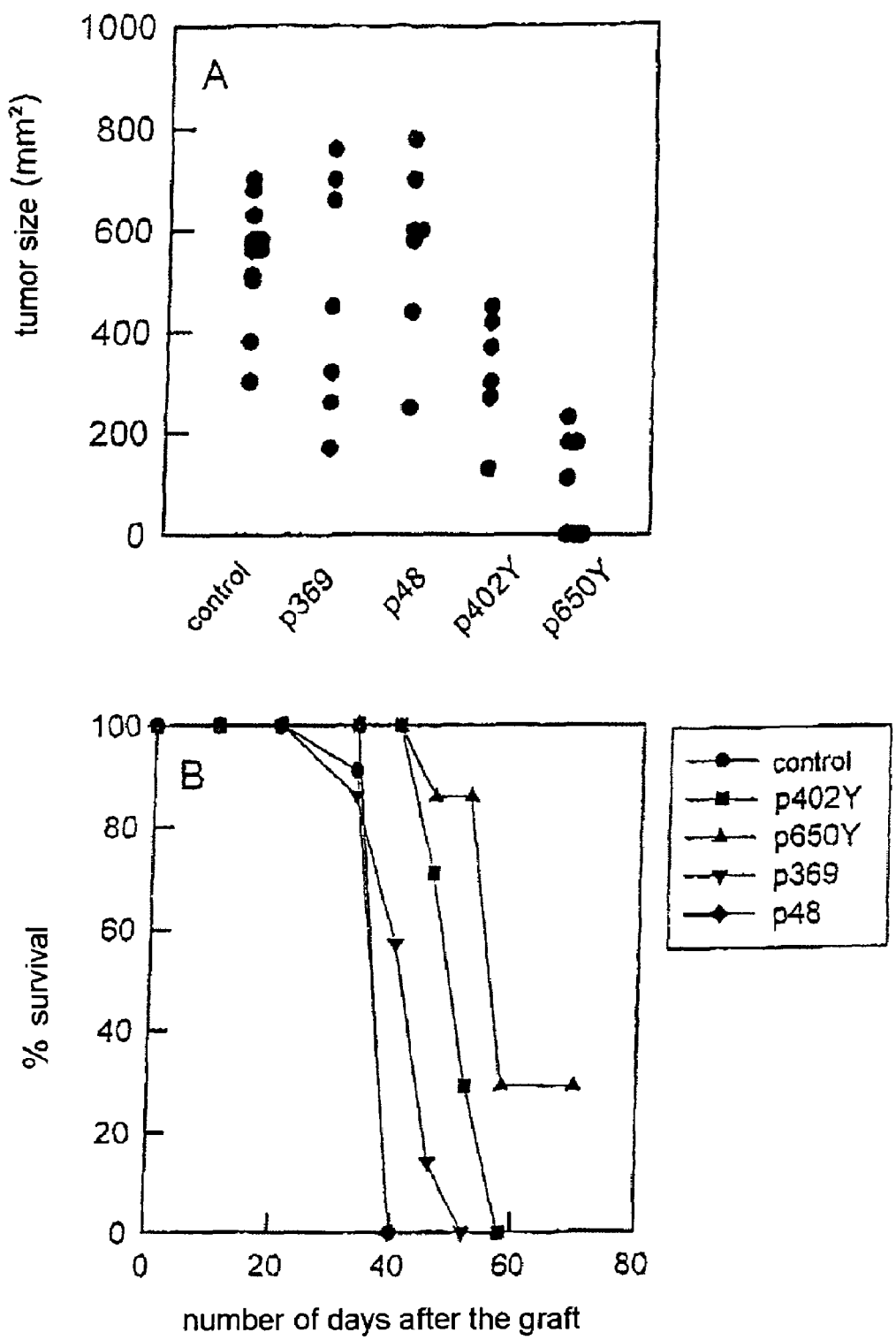
FIG. 12A is a graph illustrating tumor size as a function of the peptides used.
FIG. 12B is a graph illustrating percent survival as a function of the number of days after implantation of the tumor cells.

The effectiveness of the antitumor protection is evaluated by measuring the size of the tumors 28 days after implantation thereof (FIG. 12A: tumor size as a function of the peptides used for the vaccination) and by the survival of the grafted mice (FIG. 12B: percentage survival as a function of the number of days after implantation of the tumor cells).

The results show that, at D28, the tumors measure 560±93 mm$^2$, 474±234 mm$^2$ and 564±174 mm$^2$, respectively, in the untreated (control) mice and in the mice treated with the HER-2/neu 369 and HER-2/neu 48 peptides, but that in the batch of mice vaccinated with the HER-2/neu 402Y1 and HER-2/neu 650Y1 peptides, the tumors measure 323±116 mm$^2$ and 100±99 mm$^2$, respectively, and that 4 mice vaccinated with HER-2/neu 650Y1 show no tumors at D28.

All the unvaccinated mice die at D40 (FIG. 12B: ●).

For the mice vaccinated with the HER-2/neu 369 and HER-2/neu 48 peptides (FIG. 12B: ▼ and ♦), mortality only appears at D32 and the final mouse dies at D52.

The mortality is significantly reduced in the batch of mice vaccinated with HER-2/neu 402Y1 and HER-2/neu 650Y1 (FIG. 12B: ■ and ▲). It is only observed from D46, and 3 mice (30%) are still alive at D70 (FIG. 12B: ▲).

This set of results demonstrates that only the forms of subdominant/cryptic peptides substituted at P1 with a tyrosine (HER-2/neu 650Y1, HER-2/neu 402Y1, mhp 572Y1 and mhp 988Y1) are capable of generating an effective antitumor response in vivo. It therefore appears to be advantageous to use, in antitumor immunotherapy, subdominant/cryptic peptides in the form in which they are substituted at P1 with a tyrosine.

EXAMPLE 7

Antitumor Activity Induced by DNA Vaccines Encoding Multiple Dominant and Subdominant/Cryptic Epitopes Derived from HER-2/neu In order to overcome the relative failures of the clinical trials carried out to date exclusively using tumor peptides, a novel approach in antitumor immunotherapy consists in inducing multispecific responses by genetic immunization with a polyepitope construct composed of eight dominant epitopes and four subdominant/cryptic epitopes which are derived from HER-2/neu and are HLA A2.1 restricted.

Selection of Epitopes

The eight dominant epitopes (HER-2/neu 799, HER-2/neu 369, HER-2/neu 789, HER-2/neu 689, HER-2/neu 773, HER-2/neu 5, HER-2/neu 48 and HER-2/neu 1023) exhibit a great affinity for HLA A2.1 (RA<5 and $DC_{50}$>4 hours), except HER-2/neu 1023, which is considered to have intermediate binding affinity (RA>5, $DC_{50}$>4 hours) (cf. table II, example 1).

The four subdominant/cryptic epitopes (HER-2/neu 466, HER-2/neu 402, HER-2/neu 391 and HER-2/neu 650) (cf. table II, example 1) exhibit a very low binding affinity and are nonimmunogenic in the HHD mice or in humans, whereas the P1Y variants (HER-2/neu 466Y, HER-2/neu 402Y1, HER-2/neu 391Y and HER-2/neu 650Y1), obtained as described in example 2, exhibit a great affinity for HLA A2.1 (RA<4 and $DC_{50}$>4 hours). These P1Y variants are given in table IX below:

TABLE IX

| P1Y variants | Sequence | RA | DC50 (hours) |
|---|---|---|---|
| HER-2/neu 466Y1 | YLIHHNTHL (SEQ ID NO:66) | 1.4 | 6 |
| HER-2/neu 402Y1 | YLEEITGYL (SEQ ID NO:67) | 3.7 | 4 |
| HER-2/neu 391Y1 | YLQPEQLQV (SEQ ID NO:68) | 1.3 | 8 |
| HER-2/neu 650Y1 | YLTSIISAV (SEQ ID NO:69) | 0.2 | 6 |

The immunogenicity of the P1Y variants and of the immunodominant epitopes is tested according to the protocol described in example 1:

Mice are vaccinated subcutaneously with each of the twelve peptides mentioned above, in the presence of the Iab Th epitope derived from the "core" antigen of HBV. Eleven days later, their spleen cells are restimulated in vitro with the peptide to be tested (1 μg), for six days, and the CTLs generated are tested against RMAS-HHD target cells loaded with the immunizing peptides or a control peptide.

Figure 13:
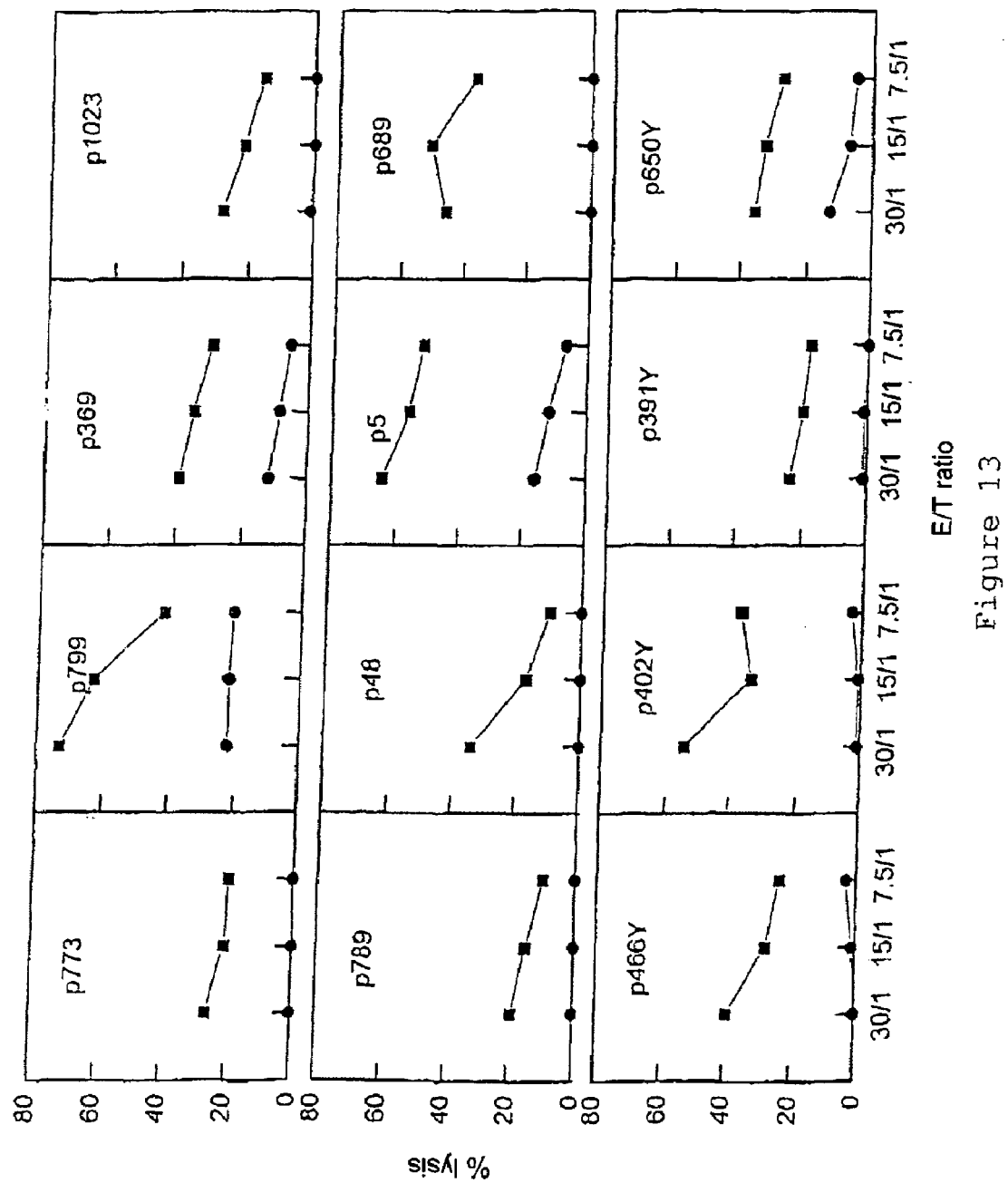

The results (% lysis as a function of the effector cell/target cell ratio) are given in FIG. 13:
RMAS-HHD cells loaded with the immunizing peptide: ■
RMAS-HHD cells loaded with a control peptide: ●.

As expected, all these epitopes cause a CTL response, and those caused by the P1Y variants are specific for the corresponding natural peptides.

Selection of a Polyepitope Construct

The polyepitope construct (pet-neu) comprises a continuous series of the abovementioned 12 epitopes, namely:
the eight dominant epitopes (HER-2/neu 799, HER-2/neu 369, HER-2/neu 789, HER-2/neu 689, HER-2/neu 773, HER-2/neu 5, HER-2/neu 48 and HER-2/neu 1023) described as being targets for tumor-infiltrating lymphocytes (TILs) in lung, ovarian, stomach and RCC cancers, and
the four subdominant/cryptic P1Y variants (HER-2/neu 466Y, HER-2/neu 402Y1, HER-2/neu 391Y and HER 650Y1) obtained as described in example 2.

The use of the polyepitope construct above was optimized for expression in humans, and any potential initiation codon was conserved as close as possible to the initiation site, in particular if Kozak sequences are incorporated. An SV5-pk tag is added at the 3' end of the construct in order to allow verification of pet-neu expression in the transfected COS cells (expression of the antibody against PK having 14 amino acids).

A 3.0 kb plasmid, Vax1 (Invitrogen), is selected, in which the sequences not required for replication in *E. coli* or for expression of the recombinant protein in mammalian cells have been removed so as to limit the DNA sequences homologous to the human genome, in order to minimize the possibility of chromosomal integration. This plasmid comprises the gene for resistance to kanamycin, rather than to ampicillin, since aminoglycosides are less liable to cause an allergic response in humans. The expression is directed by the promoter-activator sequences of the human cytomegalovirus (CMV). Efficient transcription termination and polyadenylation of the mRNA are obtained using the bovine growth hormone polyadenylation signal.

The pet-neu DNA is synthesized and cloned into the vector pVax1 (Vax1/pet-neu).

The polyepitope construct as described above has the following properties:
a) it allows the processing of each epitope at its C-terminal end, and
b) it does not create any new junctional peptides with a high affinity for the HLA A2.1 molecule.

The processing at the C-terminal end is evaluated using two models for prediction of proteasome cleavage (netChop1.0, www.cbs.dtu.dk/services/NetChopPAPROC, www.uni-tuebingen.de/uni:bcm/kuttler/links/html). A prediction of cleavage by two models is necessary in order to consider that an epitope is processed. The affinity of the new junctional peptides is evaluated as set aside in example 1 using the BIMAS prediction model [PARKER et al., J. Immunol., 152, 163, (1994)]. Among the various arrangements evaluated, the arrangement of FIG. 14, corresponding to SEQ ID No. 70, was chosen since it corresponds more closely to the two properties specified above. The HER-2/neu 773, HER-2/neu 1023, HER-2/neu 5, HER-2/neu 466Y, HER-2/neu 391Y and HER-2/neu 650Y1 peptides are predicted as being processed, and only five new junctional peptides with a high affinity for the HLA A2.1 molecule might be generated ($p67_9$, $p94_9$, $p17_9$, $p91_{10}$, $p63_{10}$); these peptides are defined by their position in the pet-neu sequence (positions: 67, 94, 17, 91 and 63) and their length (9 or 10 amino acids).

I. Immunogenicity of Vax1/pet-neu in HHD Transgenic Mice

A. Ability of Vax1/pet-neu to Induce Specific CTLs in vivo

The immunogenicity of Vax1/pet-neu is tested as described in example 1:

HHD mice, generated as described in example 1, are immunized intramuscularly at a rate of two injections, 15 days apart, with Vax1/pet-neu (150 μg). One week after the final immunization, their spleen cells are restimulated in vitro with B cells activated with LPS and loaded with each of the twelve peptides.

The cytotoxicity is evaluated using RMAS-HHD cells (target cells) loaded with the peptide corresponding to that with which the B cells were loaded or with a control peptide.

Figure 14:
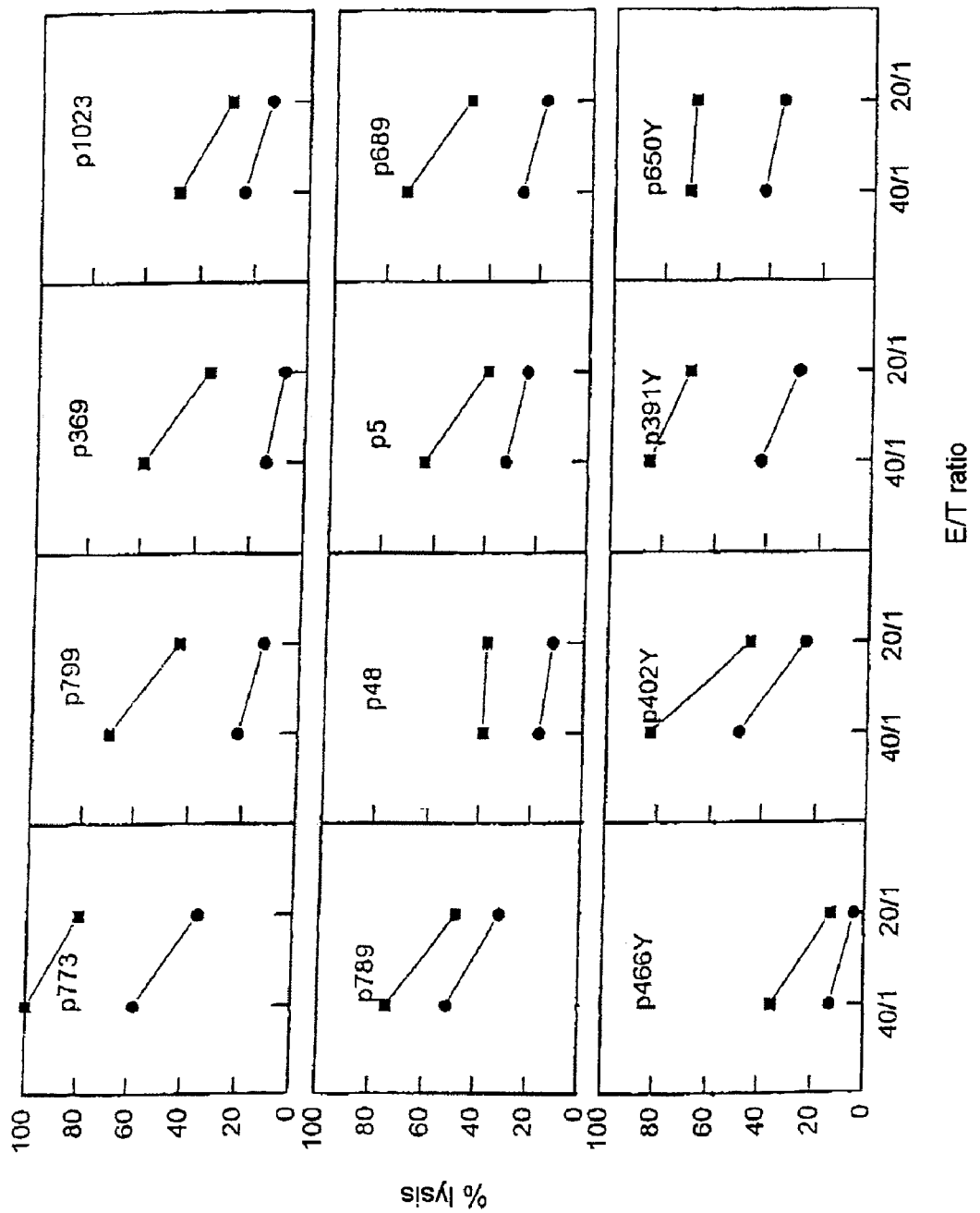

The results from an immunized HHD mouse taken randomly are given in FIG. 14 (% lysis as a function of the effector cell/target cell ratio).
RMAS-HHD cells loaded with the peptide used for the B cells: ■
RMAS-HHD cells loaded with a control peptide: ●.

The CTLs kill the RMAS-HHD cells loaded with each of the twelve peptides, although, for CTLs specific for certain peptides, lysis of the RMAS-HHD target cells loaded with a control peptide is observed (nonspecific lysis).

The greatest specific lyses (30% above background noise) are obtained with HER-2/neu 773, HER-2/neu 799, HER-2/neu 369, HER-2/neu 689, HER-2/neu 402Y1 and HER-2/neu 391Y.

B. Ability of the CTLs to Recognize Endogenous HER-2/neu

The CTLs induced in HHD mice vaccinated with Vax1/pet-neu are tested for their ability to specifically recognize endogenous HER-2/neu.

Figure 15:
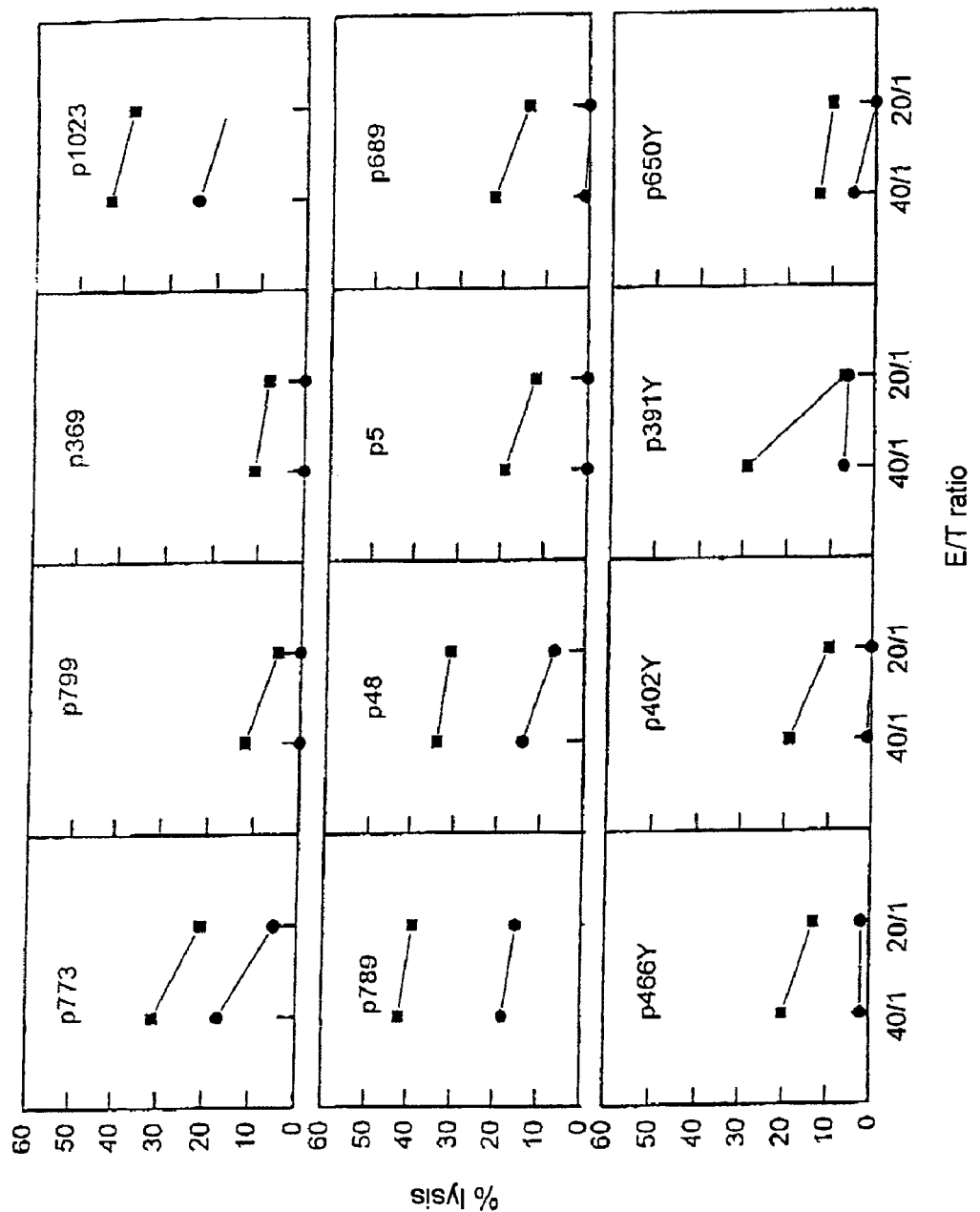

The results are given in FIG. 15 (% lysis as a function of the effector cell (E)/target cell (T) ratio).

The CTLs are induced as described in A above and are tested against the EL-4/HHD target cells (●) referenced in example 6 and the EL-4/HHD/neu target cells (■) obtained by transfecting the EL-4/HHD cells with the cDNA encoding HER-2/neu.

The CTLs specific for the twelve pet-neu peptides recognize and kill the EL-4/HHD/neu targets expressing HER-2/neu, but not the EL-4/HHD targets used as a negative control.

For the three mice tested, greater specific lysis (>20% above background noise) is obtained for HER-2/neu 1023, HER-2/neu 789, HER-2/neu 48, HER-2/neu 689, HER-2/neu 466Y, HER-2/neu 402Y1 and HER-2/neu 391Y.

C. Factor in Question in the CTL Induction

The CTL induction requires either sensitization with Vax1/pet-neu or else results from repetition of the stimulations in vitro of the naive spleen cells.

The immunogenicity of Vax1/pet-neu is tested as described in example 1:

Six mice are immunized with either the Vax1/pet-neu construct or the vector Vax1. Their spleen cells are stimulated in vitro in a repeated manner with the B cells activated with LPS and loaded with each peptide to be tested (effector cells).

The target cells used to study the specificity of the CTLs with respect to HER-2/neu are RMAS-HHD cells, and the EL-4/HHD/neu cells obtained as described in example 6.

The cytotoxicity is tested after the third stimulation in vitro. The RMAS-HHD cells, loaded with the peptide corresponding to that with which the B cells were loaded, or with a control peptide, and the EL-4/HHD/neu cells are used as target cells.

Figure 16:
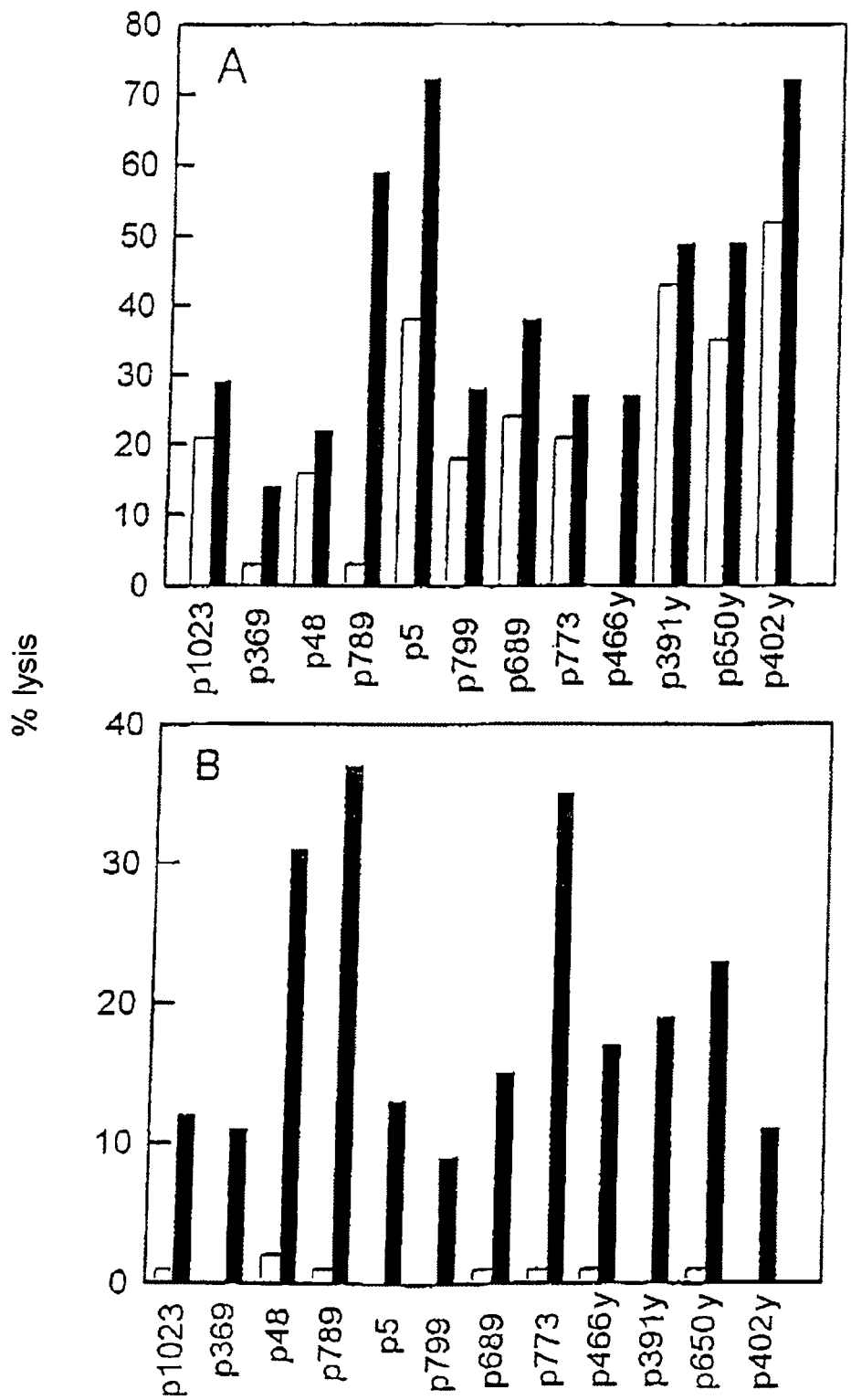

The results are given in FIG. 16 [% specific lysis (the lysis of the target cells loaded with a control peptide is deducted) after immunization with Vax1 (□) or Vax1/pet-neu (■)].

The spleen cells sensitized with Vax1/pet-neu produce specific CTLs for the twelve peptides. Surprisingly, the CTLs against the majority of the peptides, except HER-2/neu 369 and HER-2/neu 789, are generated from the spleen cells sensitized with the vector Vax1. For some peptides (HER-2/neu 1023, HER-2/neu 48, HER-2/neu 799, HER-2/neu 773, HER-2/neu 391Y), the cytotoxicity of the CTLs induced from the spleen cells sensitized with Vax1 is almost as high as the cytotoxicity of the CTLs induced from the spleen cells sensitized with Vax1/pet-neu (FIG. 16A). This demonstrates that the repeat in vitro stimulations are sufficient to trigger the CTL induction.

However, these CTLs, although they eliminate targets loaded with the peptides, are incapable of recognizing and eliminating target cells expressing endogenous HER-2/neu (EL-4/HHD/neu), contrary to the CTLs induced from the spleen cells sensitized with Vax1/pet-neu (FIG. 16B).

This set of results demonstrates that the CTLs specific for HER-2/neu capable of effectively eliminating the tumor cells expressing the antigen are generated by Vax1/pet-neu vaccination.

II. Vax1/pet-neu Vaccination Induces Antitumor Immunity in vivo

The results obtained in vitro led to an investigation of whether the Vax1/pet-neu vaccination induces protective antitumor immunity in vivo.

A. Effect on Tumor Growth and Specificity of the Antitumor Protection

An extremely tumorigenic subclone of the EL-4/HHD/neu cells, generated as described in example 6, is obtained after three in vivo selections in the HHD mice. It expresses HHD and HER-2/neu at the same level as the parental cells.

HHD mice, generated as described in example 1, are immunized at a rate of 2 injections two weeks apart, with the Vax1/pet-neu construct (FIGS. 17A and 17C) or with the empty vector Vax1 (FIG. 17B), or are not immunized (FIG. 17D).

One week after the final immunization, $2 \times 10^4$ EL-4/HHD/neu cells (FIGS. 17A, 17B and 17D) or EL-4/HHD/Tel-Am1 cells, obtained by transfecting the EL-4/HHD cells with the cDNA encoding the recombinant protein Tel-Am1, are grafted into the mice above in order to test, in vivo, the specificity of the protective antitumor immunity.

Tumor growth is evaluated every 5 to 7 days until D28, when all the unvaccinated mice are dead and the mice of the remaining groups are monitored for their mortality.

Figure 17:
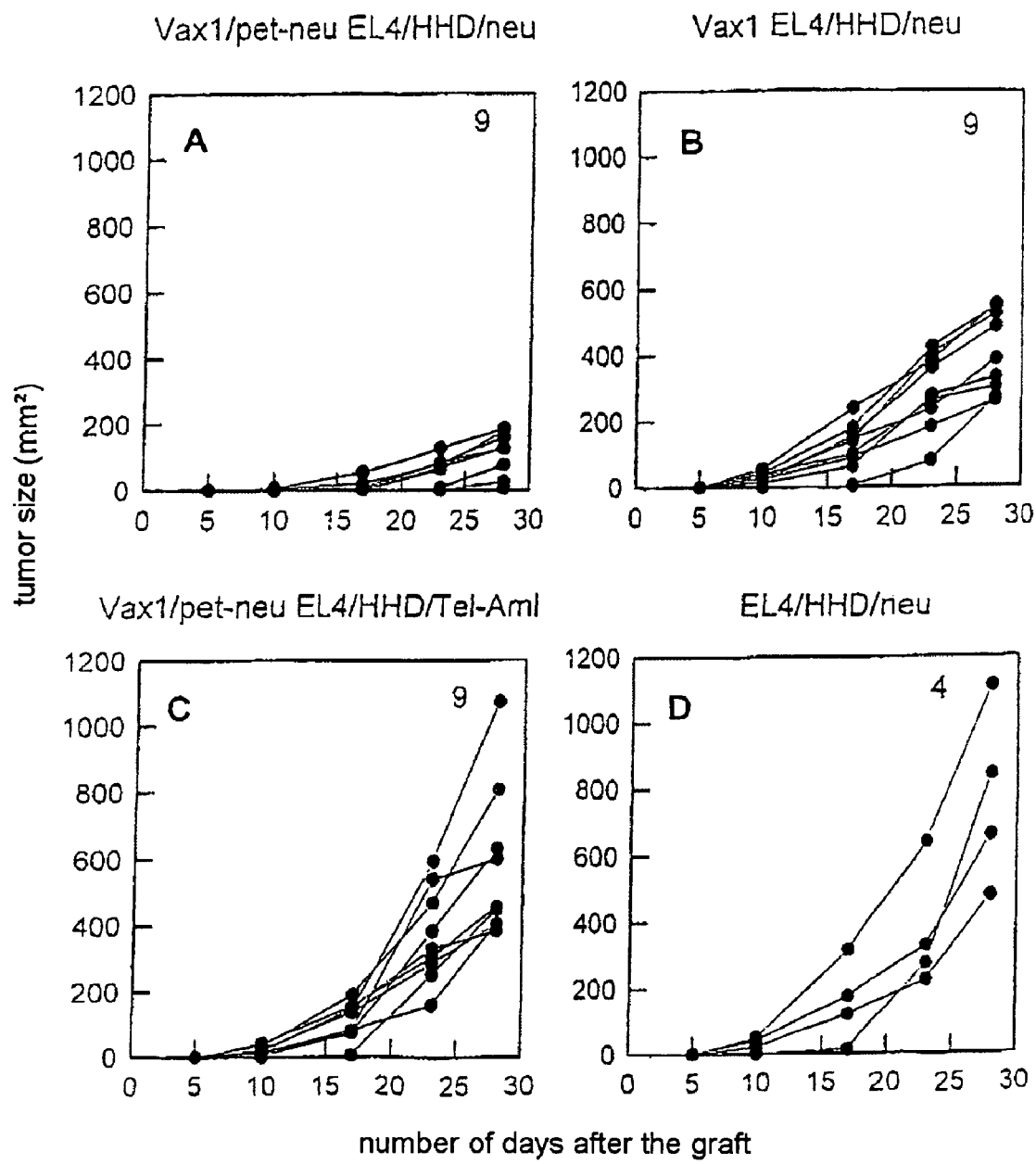
FIGS. 17A-17D are graphs illustrating tumor size as a function of the number of days after implantation of the tumor cells.

The results are given in FIG. 17 (tumor size as a function of the number of days after implantation of the tumor cells).

All the unvaccinated control mice (FIG. 17D) or mice vaccinated with Vax1 (FIG. 17B) develop tumors which appear at D17 and increase in size very rapidly. At D28, the tumors measure $772 \pm 268$ mm$^2$ and $404 \pm 121$ mm$^2$ in the control mice and the mice treated with Vax1 respectively ($p=0.04$).

On the other hand, in the batch of mice vaccinated with Vax1/pet-neu (FIG. 17A), 2 mice out of 9 do not exhibit any tumors at D28, otherwise the tumors appear at D23 and increase in size slowly. The size of the tumors is $116 \pm 66$ mm$^2$ ($p=0.0001$ by comparison with either the untreated mice or the mice treated with Vax1).

This protective antitumor immunity in vivo is specific for HER-2/neu since the mice vaccinated with Vax1/pet-neu are not protected against the EL-4/HHD/Tel-Am1 tumor (FIG. 17C). Specifically, all the mice develop tumors and the size thereof at D28 is $578 \pm 231$ mm$^2$.

B. Effect on Survival of the Mice and Specificity of the Antitumor Protection

The effect of the antitumor protection induced by the Vax1/pet-neu vaccination is confirmed by examining the survival of mice bearing tumors.

HHD mice are vaccinated and given grafts as described in A. Their mortality is monitored up to D55.

Figure 18:
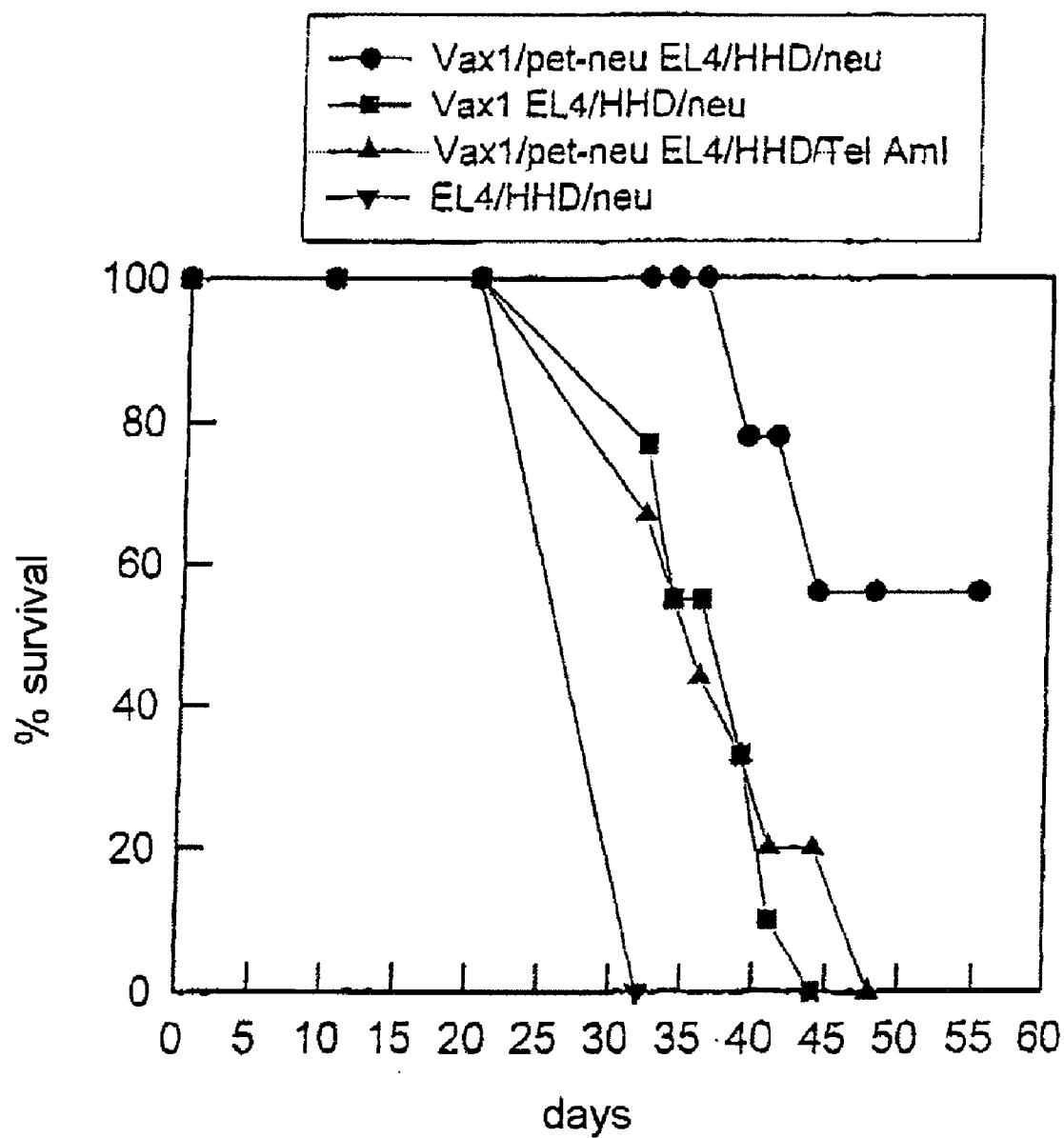
FIG. 18 is a graph illustrating percent survival as a function of the number of days after implantation of the tumor cells.

The results are given in FIG. 18 (% survival as a function of the number of days after implantation of the tumor cells).

All the unvaccinated mice die at D32 (▼).

For the mice vaccinated with Vax1 (■), the mortality begins at D32 and the last mouse dies at D42 ($p=0.04$ by comparison with the unvaccinated mice).

The mortality is significantly reduced in the batch of mice vaccinated with Vax1/pet-neu ( ). It begins at D39 and 5 mice (56%) are still alive at D55 ($p=0.0008$ by comparison with untreated mice and mice treated with Vax1).

This protective immunity is specific for HER-2/neu since the mortality of the mice treated with Vax1/pet-neu and given an EL4/HHD/Tel-Am1 tumor graft (▲) is similar to the mortality of the mice treated with Vax1 and given an EL-4/HHD/neu tumor cell graft (■).

The invention claimed is:

1. An immunogenic peptide epitope which is derived from a subdominant/cryptic epitope presented by HLA A2.1 by substitution of the N-terminal amino acid of said subdominant/cryptic epitope with a tyrosine residue, wherein said subdominant/cryptic epitope is chosen from:

the peptide HER-2/neu 650: PLTSIISAV (SEQ ID No. 4)
the peptide HER-2/neu 466: ALIHITNTHL (SEQ ID No. 5)
the peptide HER-2/neu 402: TLEEITGYL (SEQ ID No. 6)
the peptide HER-2/neu 391: PLQPEQLQV (SEQ ID No. 7)
the peptide gagp24-212: EMMTACQGV (SEQ ID No. 8)
the peptide pol79: LLDTGADDTV (SEQ ID No. 9)
the peptide mhp 572: RLFFYRKSV (SEQ ID No. 10)
the peptide mhp 988: DLQVNSLQTV (SEQ ID No. 11).

2. A composition comprising at least one immunogenic peptide epitope as claimed in claim 1.

3. The composition as claimed in claim 2, which also comprises one or more other immunogenic epitope(s).

4. The composition as claimed in claim 2, which comprises a chimeric polypeptide comprising one or more copies of an immunogenic peptide epitope derived from a subdominant/cryptic epitope presented by a class I HLA molecule.

5. The composition as claimed in claim 4, wherein said chimeric polypeptide also comprises one or more copies of one or more other immunogenic epitope(s).

6. The immunogenic peptide epitope as claimed in claim 1, which is the peptide mhp 572Y1: YLFFYRKSV (SEQ ID No. 61).

7. The composition as claimed in claim 2 and a pharmaceutically acceptable carrier.

* * * * *